(12) United States Patent  
Goldfarb et al.

(10) Patent No.: US 8,747,389 B2  
(45) Date of Patent: Jun. 10, 2014

(54) SYSTEMS FOR TREATING DISORDERS OF THE EAR, NOSE AND THROAT

(75) Inventors: Eric Goldfarb, San Francisco, CA (US); John Y. Chang, Mountain View, CA (US); William M. Facteau, Mountain View, CA (US); Sivette Lam, Santa Rosa, CA (US); Hung V. Ha, San Jose, CA (US); Isaac J. Kim, San Jose, CA (US); Ketan P. Muni, San Jose, CA (US)

(73) Assignee: Acclarent, Inc., Menlo Park, CA (US)

(*) Notice: Subject to any disclaimer, the term of this patent is extended or adjusted under 35 U.S.C. 154(b) by 292 days.

(21) Appl. No.: 11/789,704

(22) Filed: Apr. 24, 2007

(65) Prior Publication Data

US 2008/0195041 A1    Aug. 14, 2008

Related U.S. Application Data

(60) Continuation-in-part of application No. 11/355,512, filed on Feb. 16, 2006, which is a continuation-in-part of application No. 11/150,874, filed on Jun. 13, 2005, now abandoned, which is a continuation-in-part of application No. 10/944,270, filed on Sep. 17, 2004, now abandoned, which is a division of application No. 10/829,917, filed on Apr. 21, 2004, now Pat. No. 7,654,997.

(51) Int. Cl.  
*A61K 9/22* (2006.01)

(52) U.S. Cl.  
USPC .......... 604/891.1; 128/898; 604/20; 604/523; 604/22; 604/28; 604/35; 604/504; 604/509; 606/1; 606/155; 606/169; 606/195; 606/198; 606/3; 606/34; 606/41; 606/46; 606/7; 623/1.11; 623/1.13; 623/1.42

(58) Field of Classification Search  
USPC .......... 128/898; 604/20, 22, 28, 35, 504, 509, 604/523, 891.1; 606/1, 155, 169, 195, 198, 606/3, 34, 41, 46, 7; 607/46, 56, 88, 89; 623/1.11, 1.13, 1.42  
See application file for complete search history.

(56) References Cited

U.S. PATENT DOCUMENTS

| 446,173 A | 2/1891 | Hancock |
| 504,424 A | 9/1893 | De Pezzer |

(Continued)

FOREIGN PATENT DOCUMENTS

| CA | 2013323 | 9/1990 |
| CH | 668188 | 12/1988 |

(Continued)

OTHER PUBLICATIONS

Göttman, et al.; Balloon Dilation of Recurrent Ostial Occlusion of the frontal sinus; Abstract No. B-04353, European Congress of Radiology, Mar. 2001.

(Continued)

*Primary Examiner* — Nicholas Lucchesi  
*Assistant Examiner* — Scott Medway  
(74) *Attorney, Agent, or Firm* — Frost Brown Todd LLC

(57) ABSTRACT

Devices, systems and methods useable for dilating the ostia of paranasal sinuses and/or other passageways within the ear, nose or throat. A dilation catheter device and system is constructed in a manner that facilitates ease of use by the operator and, in at least some cases, allows the dilation procedure to be performed by a single operator. Additionally, the dilation catheter device and system may be useable in conjunction with an endoscope and/or a fluoroscope to provide for easy manipulation and positioning of the devices and real time visualization of the entire procedure or selected portions thereof. In some embodiments, an optional handle may be used to facilitate grasping or supporting a device of the present invention as well as another device (e.g., an endoscope) with a single hand.

30 Claims, 9 Drawing Sheets

(56) References Cited

U.S. PATENT DOCUMENTS

| | | |
|---|---|---|
| 513,667 A | 1/1894 | Buckingham |
| 705,346 A | 7/1902 | Hamilton |
| 798,775 A | 9/1905 | Forsyth |
| 816,792 A | 4/1906 | Green et al. |
| 1,080,934 A | 12/1913 | Shackleford |
| 1,200,267 A | 10/1916 | Sunnergren |
| 1,650,959 A | 11/1927 | Pitman |
| 1,735,519 A | 11/1929 | Vance |
| 1,828,986 A | 10/1931 | Stevens |
| 1,878,671 A | 9/1932 | Cantor |
| 2,201,749 A | 5/1940 | Vandegrift |
| 2,525,183 A | 3/1947 | Robison |
| 2,493,326 A | 1/1950 | Trinder |
| 2,847,997 A | 8/1958 | Tibone |
| 2,899,227 A | 8/1959 | Gschwend |
| 2,906,179 A | 9/1959 | Bower |
| 2,955,832 A | 10/1960 | Gary et al. |
| 3,009,265 A | 11/1961 | Bezark |
| 3,037,286 A | 6/1962 | Bower |
| 3,173,418 A | 3/1965 | Baran |
| 3,347,061 A | 10/1967 | Stueniky |
| 3,376,659 A | 4/1968 | Asin et al. |
| 3,384,970 A | 5/1968 | Avalear |
| 3,393,073 A | 7/1968 | Reutenauer et al. |
| 3,435,826 A | 4/1969 | Fogarty |
| 3,447,061 A | 5/1969 | Russell |
| 3,469,578 A | 9/1969 | Bierman |
| 3,481,043 A | 12/1969 | Esch |
| 3,486,539 A | 12/1969 | Jacuzzi |
| 3,506,005 A | 4/1970 | Gilio et al. |
| 3,509,638 A | 5/1970 | Macleod |
| 3,515,888 A | 6/1970 | Lewis |
| 3,527,220 A | 9/1970 | Summers |
| 3,531,868 A | 10/1970 | Stevenson |
| 3,552,384 A | 1/1971 | Pierie et al. |
| 3,624,661 A | 11/1971 | Shebanow et al. |
| 3,731,963 A | 5/1973 | Pond |
| 3,766,924 A | 10/1973 | Pidgeon |
| 3,792,391 A | 2/1974 | Ewing |
| 3,800,788 A | 4/1974 | White |
| 3,802,096 A | 4/1974 | Matern |
| 3,804,081 A | 4/1974 | Kinoshita |
| 3,834,394 A * | 9/1974 | Hunter et al. ............ 606/195 |
| 3,847,145 A | 11/1974 | Grossan |
| 3,850,176 A | 11/1974 | Gottschalk |
| 3,856,000 A | 12/1974 | Chikama |
| 3,859,993 A | 1/1975 | Bitner |
| 3,871,365 A | 3/1975 | Chikama |
| 3,894,538 A | 7/1975 | Richter |
| 3,903,893 A | 9/1975 | Scheer |
| 3,910,617 A | 10/1975 | Scalza et al. |
| 3,921,636 A | 11/1975 | Zaffaroni |
| 3,948,254 A | 4/1976 | Zaffaroni |
| 3,948,262 A | 4/1976 | Zaffaroni |
| 3,967,618 A | 7/1976 | Zaffaroni |
| 3,993,069 A | 11/1976 | Buckles et al. |
| 3,993,072 A | 11/1976 | Zaffaroni |
| 3,993,073 A | 11/1976 | Zaffaroni |
| 4,016,251 A | 4/1977 | Higuchi et al. |
| 4,052,505 A | 10/1977 | Higuchi et al. |
| 4,053,975 A | 10/1977 | Olbrich |
| 4,069,307 A | 1/1978 | Higuchi et al. |
| 4,102,342 A | 7/1978 | Akiyama et al. |
| 4,138,151 A | 2/1979 | Nakao |
| 4,184,497 A | 1/1980 | Kolff et al. |
| 4,198,766 A | 4/1980 | Camin |
| 4,207,890 A | 6/1980 | Mamajek et al. |
| 4,209,919 A | 7/1980 | Kirikae et al. |
| 4,213,095 A | 7/1980 | Falconer |
| 4,217,898 A | 8/1980 | Theeuwes |
| 4,268,115 A | 5/1981 | Slemon et al. |
| 4,299,226 A * | 11/1981 | Banka ..................... 604/509 |
| 4,299,227 A | 11/1981 | Lincoff |
| 4,312,353 A | 1/1982 | Shahbabian |
| 4,338,941 A | 7/1982 | Payton |
| D269,204 S | 5/1983 | Trepp |
| 4,388,941 A | 6/1983 | Riedhammer |
| RE31,351 E | 8/1983 | Falconer |
| 4,435,716 A | 3/1984 | Zandbergen |
| 4,437,856 A | 3/1984 | Valli |
| 4,450,150 A | 5/1984 | Sidman |
| 4,459,977 A | 7/1984 | Pizon et al. |
| 4,464,175 A | 8/1984 | Altman et al. |
| 4,471,779 A | 9/1984 | Antoshkiw et al. |
| 4,499,899 A | 2/1985 | Lyons, III |
| 4,554,929 A | 11/1985 | Samson et al. |
| 4,564,364 A | 1/1986 | Zaffaroni et al. |
| 4,571,239 A | 2/1986 | Heyman |
| 4,571,240 A | 2/1986 | Samson et al. |
| 4,581,017 A | 4/1986 | Sahota |
| 4,585,000 A | 4/1986 | Hershenson |
| D283,921 S | 5/1986 | Dyak |
| 4,589,868 A | 5/1986 | Dretler |
| 4,596,528 A | 6/1986 | Lewis et al. |
| D284,892 S | 7/1986 | Glassman |
| 4,603,564 A | 8/1986 | Kleinhany et al. |
| 4,606,346 A | 8/1986 | Berg et al. |
| 4,607,622 A | 8/1986 | Fritch et al. |
| 4,637,389 A | 1/1987 | Heyden |
| 4,639,244 A | 1/1987 | Rizk et al. |
| 4,645,495 A | 2/1987 | Vaillancourt |
| 4,669,469 A | 6/1987 | Gifford, III |
| 4,672,961 A | 6/1987 | Davies |
| 4,675,613 A | 6/1987 | Naegeli et al. |
| 4,691,948 A | 9/1987 | Austin, Jr. et al. |
| 4,708,434 A | 11/1987 | Tsuno |
| 4,708,834 A | 11/1987 | Cohen et al. |
| 4,726,772 A | 2/1988 | Amplatz |
| 4,736,970 A | 4/1988 | McGourty et al. |
| 4,737,141 A | 4/1988 | Spits |
| 4,748,869 A | 6/1988 | Ohtsuka |
| 4,748,969 A | 6/1988 | Wardle |
| 4,748,986 A | 6/1988 | Morrison et al. |
| 4,755,171 A | 7/1988 | Tennant |
| 4,771,776 A | 9/1988 | Powell et al. |
| 4,793,359 A | 12/1988 | Sharrow |
| 4,795,439 A | 1/1989 | Guest |
| 4,796,629 A | 1/1989 | Grayzel |
| 4,803,076 A | 2/1989 | Ranade |
| 4,811,743 A | 3/1989 | Stevens |
| 4,815,478 A | 3/1989 | Buchbinder et al. |
| 4,819,619 A | 4/1989 | Augustine et al. |
| 4,846,186 A | 7/1989 | Box et al. |
| 4,847,258 A | 7/1989 | Sturm et al. |
| 4,851,228 A | 7/1989 | Zentner et al. |
| 4,854,330 A | 8/1989 | Evans, III et al. |
| 4,862,874 A | 9/1989 | Kellner |
| 4,867,138 A * | 9/1989 | Kubota et al. ............ 600/107 |
| 4,883,465 A | 11/1989 | Brennan |
| 4,897,651 A | 1/1990 | DeMonte |
| 4,898,577 A | 2/1990 | Badger et al. |
| 4,917,419 A | 4/1990 | Mora, Jr. et al. |
| 4,917,667 A | 4/1990 | Jackson |
| 4,919,112 A | 4/1990 | Siegmund |
| 4,920,967 A | 5/1990 | Cottonaro |
| 4,925,445 A | 5/1990 | Sakamoto et al. |
| 4,940,062 A | 7/1990 | Hampton |
| 4,943,275 A | 7/1990 | Stricker |
| 4,946,466 A | 8/1990 | Pinchuk et al. |
| 4,961,433 A | 10/1990 | Christian |
| 4,966,163 A | 10/1990 | Kraus |
| 4,984,581 A | 1/1991 | Stice |
| 4,994,033 A * | 2/1991 | Shockey et al. .......... 604/101.02 |
| 4,998,916 A | 3/1991 | Hammerslag et al. |
| 4,998,917 A | 3/1991 | Gaiser |
| 5,001,825 A | 3/1991 | Halpern |
| 5,002,322 A | 3/1991 | Fukumoto |
| 5,009,655 A | 4/1991 | Daignault, Jr. et al. |
| 5,019,075 A | 5/1991 | Spears et al. |
| 5,019,372 A | 5/1991 | Folkman et al. |
| 5,020,514 A | 6/1991 | Heckele |
| 5,021,043 A | 6/1991 | Becker et al. |
| 5,024,650 A | 6/1991 | Hagiwara et al. |
| 5,024,658 A | 6/1991 | Kozlov et al. |

(56) References Cited

U.S. PATENT DOCUMENTS

| | | |
|---|---|---|
| 5,026,384 A | 6/1991 | Farr et al. |
| 5,030,227 A | 7/1991 | Rosenbluth et al. |
| 5,041,089 A | 8/1991 | Mueller et al. |
| 5,044,678 A | 9/1991 | Detweiler |
| 5,053,007 A | 10/1991 | Euteneuer |
| 5,055,051 A | 10/1991 | Duncan |
| 5,060,660 A | 10/1991 | Gambale et al. |
| 5,067,489 A | 11/1991 | Lind |
| 5,069,226 A | 12/1991 | Yamauchi et al. |
| 5,087,244 A | 2/1992 | Wolinsky et al. |
| 5,087,246 A | 2/1992 | Smith |
| 5,090,595 A | 2/1992 | Vandoninck |
| 5,090,910 A | 2/1992 | Narlo |
| 5,102,402 A | 4/1992 | Dror et al. |
| 5,112,228 A | 5/1992 | Zouras |
| 5,116,311 A | 5/1992 | Lofstedt |
| 5,127,393 A | 7/1992 | McFarlin et al. |
| 5,137,517 A | 8/1992 | Loney et al. |
| 5,139,510 A | 8/1992 | Goldsmith, III et al. |
| 5,139,832 A | 8/1992 | Hayashi et al. |
| D329,496 S | 9/1992 | Wotton |
| 5,152,747 A | 10/1992 | Olivier |
| 5,156,595 A | 10/1992 | Adams |
| 5,163,989 A | 11/1992 | Campbell et al. |
| 5,167,220 A | 12/1992 | Brown |
| 5,168,864 A | 12/1992 | Shockey |
| 5,169,043 A | 12/1992 | Catania |
| 5,169,386 A | 12/1992 | Becker et al. |
| 5,171,233 A | 12/1992 | Amplatz et al. |
| 5,180,368 A | 1/1993 | Garrison |
| 5,183,470 A | 2/1993 | Wettermann |
| 5,189,110 A | 2/1993 | Ikematu et al. |
| 5,195,168 A | 3/1993 | Yong |
| 5,197,457 A | 3/1993 | Adair |
| 5,207,695 A | 5/1993 | Trout, III |
| 5,211,952 A | 5/1993 | Spicer et al. |
| 5,215,105 A * | 6/1993 | Kizelshteyn et al. ......... 128/898 |
| 5,221,260 A | 6/1993 | Burns et al. |
| 5,226,302 A | 7/1993 | Anderson |
| 5,230,348 A | 7/1993 | Ishibe et al. |
| 5,236,422 A | 8/1993 | Eplett, Jr. |
| 5,238,004 A | 8/1993 | Sahatjian et al. |
| 5,243,996 A | 9/1993 | Hall |
| D340,111 S | 10/1993 | Yoshikawa |
| 5,250,059 A | 10/1993 | Andreas et al. |
| 5,251,092 A | 10/1993 | Brady et al. |
| 5,252,183 A | 10/1993 | Shaban et al. |
| 5,255,679 A | 10/1993 | Imran |
| 5,256,144 A | 10/1993 | Kraus et al. |
| 5,263,926 A | 11/1993 | Wilk |
| 5,264,260 A | 11/1993 | Saab |
| 5,267,965 A | 12/1993 | Deniega |
| 5,269,752 A | 12/1993 | Bennett |
| 5,270,086 A | 12/1993 | Hamlin |
| 5,273,052 A | 12/1993 | Kraus et al. |
| 5,275,593 A | 1/1994 | Easley et al. |
| 5,286,254 A | 2/1994 | Shapland et al. |
| 5,290,310 A | 3/1994 | Makower et al. |
| 5,295,694 A | 3/1994 | Levin |
| 5,300,085 A * | 4/1994 | Yock ............................ 606/191 |
| 5,304,123 A | 4/1994 | Atala et al. |
| 5,308,326 A | 5/1994 | Zimmon |
| 5,312,430 A | 5/1994 | Rosenbluth et al. |
| 5,313,967 A | 5/1994 | Lieber et al. |
| 5,314,408 A | 5/1994 | Salmon et al. |
| 5,314,417 A | 5/1994 | Stephens et al. |
| 5,315,618 A | 5/1994 | Yoshida |
| 5,318,528 A | 6/1994 | Heaven et al. |
| 5,324,306 A | 6/1994 | Makower et al. |
| 5,333,620 A | 8/1994 | Moutafis et al. |
| 5,334,167 A | 8/1994 | Cocanower |
| 5,334,187 A | 8/1994 | Fischell et al. |
| 5,335,671 A | 8/1994 | Clement |
| 5,336,163 A | 8/1994 | DeMane et al. |
| 5,341,818 A | 8/1994 | Abrams et al. |
| 5,342,296 A | 8/1994 | Persson et al. |
| 5,343,865 A | 9/1994 | Gardineer et al. |
| 5,345,945 A | 9/1994 | Hodgson et al. |
| 5,346,075 A | 9/1994 | Nichols et al. |
| 5,346,508 A | 9/1994 | Hastings |
| 5,348,537 A | 9/1994 | Wiesner et al. |
| 5,350,396 A | 9/1994 | Eliachar |
| 5,356,418 A | 10/1994 | Shturman |
| 5,368,049 A | 11/1994 | Raman et al. |
| 5,368,558 A | 11/1994 | Nita |
| 5,368,566 A | 11/1994 | Crocker |
| 5,372,138 A | 12/1994 | Crowley et al. |
| 5,372,584 A | 12/1994 | Zink et al. |
| D355,031 S | 1/1995 | Yoshikawa |
| 5,386,817 A | 2/1995 | Jones |
| 5,391,147 A | 2/1995 | Imran et al. |
| 5,391,179 A | 2/1995 | Mezzoli |
| 5,402,799 A | 4/1995 | Colon et al. |
| 5,409,444 A | 4/1995 | Kensey et al. |
| 5,411,475 A | 5/1995 | Atala et al. |
| 5,411,476 A | 5/1995 | Abrams et al. |
| 5,411,477 A | 5/1995 | Saab |
| 5,415,633 A | 5/1995 | Lazarus |
| 5,425,370 A | 6/1995 | Vilkomerson |
| 5,439,446 A | 8/1995 | Barry |
| 5,441,494 A | 8/1995 | Ortiz |
| 5,441,497 A | 8/1995 | Narciso, Jr. |
| 5,445,646 A | 8/1995 | Euteneuer et al. |
| 5,450,853 A | 9/1995 | Hastings et al. |
| 5,451,221 A | 9/1995 | Cho et al. |
| 5,454,817 A | 10/1995 | Katz |
| 5,458,572 A | 10/1995 | Campbell et al. |
| 5,459,700 A | 10/1995 | Jacobs |
| 5,465,717 A | 11/1995 | Imran et al. |
| 5,465,733 A | 11/1995 | Hinohara et al. |
| 5,478,565 A | 12/1995 | Geria |
| 5,486,181 A | 1/1996 | Cohen et al. |
| 5,496,338 A | 3/1996 | Miyagi et al. |
| 5,497,783 A | 3/1996 | Urick et al. |
| 5,507,301 A | 4/1996 | Wasicek et al. |
| 5,507,725 A | 4/1996 | Savage et al. |
| 5,507,766 A | 4/1996 | Kugo et al. |
| 5,507,795 A | 4/1996 | Chiang et al. |
| 5,512,055 A | 4/1996 | Domb et al. |
| 5,514,128 A | 5/1996 | Hillsman et al. |
| 5,519,532 A | 5/1996 | Broome |
| 5,531,676 A | 7/1996 | Edwards et al. |
| 5,533,985 A | 7/1996 | Wong |
| 5,538,008 A | 7/1996 | Crowe |
| 5,546,964 A | 8/1996 | Stangerup |
| 5,549,542 A | 8/1996 | Kovalcheck |
| 5,558,073 A | 9/1996 | Pomeranz et al. |
| 5,558,652 A | 9/1996 | Henke |
| 5,562,619 A | 10/1996 | Mirarchi et al. |
| 5,568,809 A | 10/1996 | Ben-Haim |
| 5,571,086 A | 11/1996 | Kaplan et al. |
| 5,578,007 A | 11/1996 | Imran |
| 5,578,048 A | 11/1996 | Pasqualucci et al. |
| 5,582,575 A | 12/1996 | Heckele et al. |
| 5,584,827 A | 12/1996 | Korteweg et al. |
| 5,591,194 A | 1/1997 | Berthiaume |
| 5,599,284 A | 2/1997 | Shea |
| 5,599,304 A | 2/1997 | Shaari |
| 5,599,576 A | 2/1997 | Opolski |
| 5,601,087 A | 2/1997 | Gunderson et al. |
| 5,601,594 A | 2/1997 | Best |
| 5,607,386 A | 3/1997 | Flam |
| 5,617,870 A | 4/1997 | Hastings et al. |
| 5,626,374 A | 5/1997 | Kim |
| 5,633,000 A | 5/1997 | Grossman et al. |
| 5,634,908 A | 6/1997 | Loomas |
| 5,638,819 A | 6/1997 | Manwaring et al. |
| 5,643,251 A | 7/1997 | Hillsman et al. |
| 5,645,789 A | 7/1997 | Roucher, Jr. |
| 5,647,361 A | 7/1997 | Damadian |
| 5,656,030 A | 8/1997 | Hunjan et al. |
| 5,662,674 A | 9/1997 | Debbas |
| 5,664,567 A | 9/1997 | Linder |
| 5,664,580 A | 9/1997 | Erickson et al. |

(56) References Cited

U.S. PATENT DOCUMENTS

| | | | |
|---|---|---|---|
| 5,665,052 A | 9/1997 | Bullard |
| 5,669,388 A | 9/1997 | Vilkomerson |
| 5,673,707 A | 10/1997 | Chandrasekaran |
| 5,676,673 A | 10/1997 | Ferre et al. |
| 5,679,400 A | 10/1997 | Tuch |
| 5,682,199 A | 10/1997 | Lankford |
| 5,685,838 A | 11/1997 | Peters et al. |
| 5,685,847 A | 11/1997 | Barry |
| 5,690,373 A | 11/1997 | Luker |
| 5,693,065 A | 12/1997 | Rains, III |
| 5,694,945 A | 12/1997 | Ben-Haim |
| 5,697,159 A | 12/1997 | Linden |
| 5,700,286 A | 12/1997 | Tartaglia et al. |
| 5,707,376 A | 1/1998 | Kavteladze et al. |
| 5,707,389 A | 1/1998 | Louw et al. |
| 5,708,175 A | 1/1998 | Koyanagi et al. |
| 5,711,315 A | 1/1998 | Jerusalmy |
| 5,713,839 A | 2/1998 | Shea |
| 5,713,946 A | 2/1998 | Ben-Haim |
| 5,718,702 A | 2/1998 | Edwards |
| 5,720,300 A | 2/1998 | Fagan et al. |
| 5,722,401 A | 3/1998 | Pietroski et al. |
| 5,722,984 A | 3/1998 | Fischell et al. |
| 5,729,129 A | 3/1998 | Acker |
| 5,730,128 A | 3/1998 | Pomeranz et al. |
| 5,733,248 A | 3/1998 | Adams et al. |
| 5,752,513 A | 5/1998 | Acker et al. |
| 5,762,604 A | 6/1998 | Kieturakis |
| 5,766,158 A | 6/1998 | Opolski |
| 5,775,327 A | 7/1998 | Randolph et al. |
| 5,776,158 A | 7/1998 | Chou |
| 5,779,699 A | 7/1998 | Lipson |
| 5,789,391 A | 8/1998 | Jacobus et al. |
| 5,792,100 A | 8/1998 | Shantha |
| 5,797,878 A | 8/1998 | Bleam |
| 5,803,089 A | 9/1998 | Ferre et al. |
| 5,814,016 A | 9/1998 | Valley et al. |
| 5,819,723 A | 10/1998 | Joseph |
| 5,820,568 A | 10/1998 | Willis |
| 5,824,044 A | 10/1998 | Quiachon et al. |
| 5,824,048 A | 10/1998 | Tuch |
| 5,824,173 A * | 10/1998 | Fontirroche et al. ............ 156/86 |
| 5,827,224 A | 10/1998 | Shippert |
| 5,830,188 A | 11/1998 | Abouleish |
| 5,833,608 A | 11/1998 | Acker |
| 5,833,645 A | 11/1998 | Lieber et al. |
| 5,833,650 A | 11/1998 | Imran |
| 5,833,682 A | 11/1998 | Amplatz et al. |
| 5,836,638 A | 11/1998 | Slocum |
| 5,836,935 A | 11/1998 | Ashton et al. |
| 5,837,313 A | 11/1998 | Ding et al. |
| 5,843,089 A | 12/1998 | Sahatjian et al. |
| 5,843,113 A | 12/1998 | High |
| 5,846,259 A | 12/1998 | Berthiaume |
| 5,857,998 A | 1/1999 | Barry |
| 5,862,693 A | 1/1999 | Myers et al. |
| 5,865,767 A | 2/1999 | Frechette et al. |
| 5,872,879 A | 2/1999 | Hamm |
| 5,873,835 A | 2/1999 | Hastings et al. |
| 5,879,324 A | 3/1999 | von Hoffmann |
| 5,887,467 A | 3/1999 | Butterweck et al. |
| 5,902,247 A | 5/1999 | Coe et al. |
| 5,902,333 A * | 5/1999 | Roberts et al. ................ 606/191 |
| 5,904,701 A | 5/1999 | Daneshvar |
| 5,908,407 A | 6/1999 | Frazee et al. |
| 5,916,193 A | 6/1999 | Stevens et al. |
| 5,928,192 A | 7/1999 | Maahs |
| 5,931,811 A | 8/1999 | Haissaguerre et al. |
| 5,931,818 A | 8/1999 | Werp et al. |
| 5,932,035 A | 8/1999 | Koger et al. |
| 5,935,061 A | 8/1999 | Acker et al. |
| 5,941,816 A | 8/1999 | Barthel et al. |
| D413,629 S | 9/1999 | Wolff |
| 5,947,988 A | 9/1999 | Smith |
| 5,949,929 A | 9/1999 | Hamm |
| 5,954,693 A | 9/1999 | Barry |
| 5,954,694 A | 9/1999 | Sunseri |
| 5,957,842 A | 9/1999 | Littmann et al. |
| 5,968,085 A | 10/1999 | Morris et al. |
| 5,971,975 A | 10/1999 | Mills et al. |
| 5,979,290 A | 11/1999 | Simeone |
| 5,980,503 A | 11/1999 | Chin |
| 5,980,551 A | 11/1999 | Summers et al. |
| 5,984,945 A | 11/1999 | Sirhan |
| 5,985,307 A | 11/1999 | Hanson et al. |
| 5,997,562 A | 12/1999 | Zadno-Azizi |
| 6,006,126 A | 12/1999 | Cosman |
| 6,006,130 A | 12/1999 | Higo et al. |
| 6,007,516 A | 12/1999 | Burbank et al. |
| 6,007,991 A | 12/1999 | Sivaraman et al. |
| 6,010,511 A | 1/2000 | Murphy |
| 6,013,019 A | 1/2000 | Fischell et al. |
| 6,015,414 A | 1/2000 | Werp et al. |
| 6,016,429 A | 1/2000 | Khafizov et al. |
| 6,016,439 A | 1/2000 | Acker |
| 6,019,736 A | 2/2000 | Avellanet et al. |
| 6,019,777 A | 2/2000 | Mackenzie |
| 6,021,340 A | 2/2000 | Randolph et al. |
| 6,022,313 A | 2/2000 | Ginn et al. |
| 6,027,461 A | 2/2000 | Walker et al. |
| 6,027,478 A | 2/2000 | Katz |
| 6,039,699 A | 3/2000 | Viera |
| 6,042,561 A | 3/2000 | Ash et al. |
| 6,048,299 A | 4/2000 | von Hoffmann |
| 6,048,358 A | 4/2000 | Barak |
| 6,053,172 A | 4/2000 | Hovda et al. |
| 6,056,702 A | 5/2000 | Lorenzo |
| 6,059,752 A | 5/2000 | Segal |
| 6,063,079 A | 5/2000 | Hovda et al. |
| 6,071,233 A | 6/2000 | Ishikawa et al. |
| 6,079,755 A | 6/2000 | Chang |
| 6,080,190 A | 6/2000 | Schwartz |
| 6,083,148 A | 7/2000 | Williams |
| 6,083,188 A | 7/2000 | Becker et al. |
| 6,086,585 A | 7/2000 | Hovda et al. |
| 6,092,846 A | 7/2000 | Fuss et al. |
| 6,093,150 A | 7/2000 | Chandler et al. |
| 6,093,195 A | 7/2000 | Ouchi |
| 6,109,268 A | 8/2000 | Thapliyal et al. |
| 6,113,567 A | 9/2000 | Becker |
| 6,117,105 A | 9/2000 | Bresnaham et al. |
| 6,122,541 A | 9/2000 | Cosman et al. |
| 6,123,697 A | 9/2000 | Shippert |
| 6,135,991 A | 10/2000 | Muni et al. |
| 6,136,006 A | 10/2000 | Johnson et al. |
| 6,139,510 A | 10/2000 | Palermo |
| 6,142,957 A | 11/2000 | Diamond et al. |
| 6,146,415 A | 11/2000 | Fitz |
| 6,148,823 A | 11/2000 | Hastings |
| 6,149,213 A | 11/2000 | Sokurenko et al. |
| 6,159,170 A | 12/2000 | Borodulin et al. |
| 6,171,298 B1 | 1/2001 | Matsuura et al. |
| 6,171,303 B1 | 1/2001 | Ben-Haim et al. |
| 6,174,280 B1 | 1/2001 | Oneda et al. |
| 6,176,829 B1 | 1/2001 | Vilkomerson |
| 6,179,788 B1 | 1/2001 | Sullivan |
| 6,179,811 B1 | 1/2001 | Fugoso et al. |
| 6,183,433 B1 | 2/2001 | Bays |
| 6,183,461 B1 | 2/2001 | Matsuura et al. |
| 6,183,464 B1 | 2/2001 | Sharp et al. |
| 6,190,353 B1 | 2/2001 | Makower et al. |
| 6,190,381 B1 | 2/2001 | Olsen et al. |
| 6,193,650 B1 | 2/2001 | Ryan, Jr. |
| 6,195,225 B1 | 2/2001 | Komatsu et al. |
| 6,200,257 B1 | 3/2001 | Winkler |
| 6,206,870 B1 | 3/2001 | Kanner |
| 6,206,900 B1 | 3/2001 | Tabatabaei et al. |
| 6,213,975 B1 | 4/2001 | Laksin |
| 6,221,042 B1 | 4/2001 | Adams |
| 6,231,543 B1 * | 5/2001 | Hegde et al. ................ 604/96.01 |
| 6,234,958 B1 | 5/2001 | Snoke et al. |
| 6,238,364 B1 | 5/2001 | Becker |
| 6,238,391 B1 | 5/2001 | Olsen et al. |
| 6,241,519 B1 | 6/2001 | Sedelmayer |

(56) References Cited

U.S. PATENT DOCUMENTS

| | | | | |
|---|---|---|---|---|
| 6,249,180 | B1 | 6/2001 | Maalej et al. | |
| 6,254,550 | B1 | 7/2001 | McNamara et al. | |
| 6,268,574 | B1 | 7/2001 | Edens | |
| 6,270,477 | B1 | 8/2001 | Bagaoisan et al. | |
| 6,290,689 | B1 | 9/2001 | Delaney et al. | |
| 6,293,957 | B1 | 9/2001 | Peters et al. | |
| 6,295,990 | B1 | 10/2001 | Lewis et al. | |
| 6,302,875 | B1 | 10/2001 | Makower et al. | |
| 6,306,105 | B1 | 10/2001 | Rooney et al. | |
| 6,306,124 | B1 | 10/2001 | Jones et al. | |
| D450,382 | S | 11/2001 | Nestenborg | |
| 6,322,495 | B1 | 11/2001 | Snow et al. | |
| 6,328,564 | B1 | 12/2001 | Thurow | |
| 6,332,089 | B1 | 12/2001 | Acker et al. | |
| 6,332,891 | B1 | 12/2001 | Himes | |
| 6,340,360 | B1 | 1/2002 | Lyles et al. | |
| 6,344,028 | B1 | 2/2002 | Barry | |
| 6,348,041 | B1 | 2/2002 | Klint | |
| 6,352,503 | B1 | 3/2002 | Matsui et al. | |
| 6,364,856 | B1 | 4/2002 | Ding et al. | |
| 6,375,615 | B1 | 4/2002 | Flaherty et al. | |
| 6,375,629 | B1 | 4/2002 | Muni et al. | |
| 6,383,146 | B1 | 5/2002 | Klint | |
| 6,386,197 | B1 | 5/2002 | Miller | |
| 6,389,313 | B1 | 5/2002 | Marchitto et al. | |
| 6,390,993 | B1 | 5/2002 | Cornish et al. | |
| 6,394,093 | B1 | 5/2002 | Lethi | |
| 6,398,758 | B1 | 6/2002 | Jacobsen et al. | |
| 6,409,863 | B1 * | 6/2002 | Williams et al. | 156/198 |
| 6,423,012 | B1 | 7/2002 | Kato et al. | |
| 6,425,877 | B1 | 7/2002 | Edwards | |
| 6,432,986 | B2 | 8/2002 | Levin | |
| 6,440,061 | B1 | 8/2002 | Wenner et al. | |
| 6,443,947 | B1 | 9/2002 | Marko et al. | |
| 6,445,939 | B1 | 9/2002 | Swanson et al. | |
| 6,450,975 | B1 | 9/2002 | Brennan et al. | |
| 6,450,989 | B2 | 9/2002 | Dubrul et al. | |
| 6,464,650 | B2 | 10/2002 | Jafari et al. | |
| 6,468,202 | B1 | 10/2002 | Irion et al. | |
| 6,468,297 | B1 | 10/2002 | Williams et al. | |
| 6,485,475 | B1 * | 11/2002 | Chelly | 604/264 |
| 6,488,653 | B1 | 12/2002 | Lombardo | |
| 6,491,940 | B1 | 12/2002 | Levin | |
| 6,494,894 | B2 | 12/2002 | Mirarchi | |
| 6,500,130 | B2 | 12/2002 | Gordon et al. | |
| 6,500,189 | B1 | 12/2002 | Lang et al. | |
| 6,503,087 | B1 | 1/2003 | Eggert et al. | |
| 6,503,185 | B1 | 1/2003 | Waksman et al. | |
| 6,511,418 | B2 | 1/2003 | Shahidi et al. | |
| 6,514,249 | B1 | 2/2003 | Maguire et al. | |
| 6,517,478 | B2 | 2/2003 | Khadem | |
| 6,524,299 | B1 | 2/2003 | Tran et al. | |
| 6,526,302 | B2 | 2/2003 | Hassett | |
| 6,527,753 | B2 | 3/2003 | Sekine et al. | |
| 6,529,756 | B1 | 3/2003 | Phan et al. | |
| 6,533,754 | B1 | 3/2003 | Hisamatsu et al. | |
| 6,536,437 | B1 | 3/2003 | Dragisic | |
| 6,537,294 | B1 | 3/2003 | Boyle et al. | |
| 6,543,452 | B1 | 4/2003 | Lavigne | |
| 6,544,223 | B1 | 4/2003 | Kokish | |
| 6,544,230 | B1 | 4/2003 | Flaherty et al. | |
| 6,549,800 | B1 | 4/2003 | Atalar et al. | |
| 6,551,239 | B2 | 4/2003 | Renner et al. | |
| 6,569,146 | B1 | 5/2003 | Werner et al. | |
| 6,569,147 | B1 | 5/2003 | Evans et al. | |
| 6,571,131 | B1 | 5/2003 | Nguyen | |
| 6,572,538 | B2 | 6/2003 | Takase | |
| 6,572,590 | B1 | 6/2003 | Stevens et al. | |
| 6,579,285 | B2 | 6/2003 | Sinofsky | |
| 6,585,639 | B1 | 7/2003 | Kotmel et al. | |
| 6,585,717 | B1 | 7/2003 | Wittenberger et al. | |
| 6,585,718 | B2 | 7/2003 | Hayzelden et al. | |
| 6,585,794 | B2 | 7/2003 | Shimoda et al. | |
| 6,589,164 | B1 | 7/2003 | Flaherty | |
| 6,596,009 | B1 | 7/2003 | Jelic | |
| 6,607,546 | B1 | 8/2003 | Murken | |
| 6,610,059 | B1 | 8/2003 | West, Jr. | |
| 6,612,999 | B2 | 9/2003 | Brennan et al. | |
| 6,613,066 | B1 | 9/2003 | Fukaya et al. | |
| 6,616,601 | B2 | 9/2003 | Hayakawa | |
| 6,616,659 | B1 | 9/2003 | de la Torre et al. | |
| 6,616,678 | B2 | 9/2003 | Nishtala et al. | |
| 6,616,913 | B1 | 9/2003 | Mautone | |
| 6,619,085 | B1 | 9/2003 | Hsieh | |
| 6,634,684 | B2 | 10/2003 | Spiessl | |
| 6,638,233 | B2 | 10/2003 | Corvi et al. | |
| 6,638,268 | B2 | 10/2003 | Niazi | |
| 6,638,291 | B1 | 10/2003 | Ferrera et al. | |
| 6,645,193 | B2 | 11/2003 | Mangosong | |
| 6,652,472 | B2 | 11/2003 | Jafari et al. | |
| 6,652,480 | B1 * | 11/2003 | Imran et al. | 604/35 |
| 6,656,166 | B2 | 12/2003 | Lurie et al. | |
| 6,659,106 | B1 | 12/2003 | Hovda et al. | |
| 6,663,589 | B1 | 12/2003 | Halevy | |
| 6,669,689 | B2 | 12/2003 | Lehmann et al. | |
| 6,669,711 | B1 | 12/2003 | Noda | |
| 6,672,773 | B1 | 1/2004 | Glenn et al. | |
| 6,673,025 | B1 | 1/2004 | Richardson et al. | |
| 6,679,871 | B2 | 1/2004 | Hahnen | |
| 6,685,648 | B2 | 2/2004 | Flaherty et al. | |
| 6,689,096 | B1 | 2/2004 | Loubens et al. | |
| 6,689,146 | B1 | 2/2004 | Himes | |
| 6,702,735 | B2 | 3/2004 | Kelly | |
| 6,712,757 | B2 | 3/2004 | Becker et al. | |
| 6,714,809 | B2 | 3/2004 | Lee et al. | |
| 6,716,183 | B2 | 4/2004 | Clayman et al. | |
| 6,716,216 | B1 | 4/2004 | Boucher et al. | |
| 6,716,813 | B2 | 4/2004 | Lim et al. | |
| 6,719,749 | B1 | 4/2004 | Schweikert et al. | |
| 6,738,656 | B1 | 5/2004 | Ferre et al. | |
| 6,755,812 | B2 | 6/2004 | Peterson et al. | |
| 6,776,772 | B1 | 8/2004 | Vrijer et al. | |
| 6,780,168 | B2 | 8/2004 | Jellie | |
| 6,783,522 | B2 | 8/2004 | Fischell | |
| 6,783,536 | B2 | 8/2004 | Vilsmeier et al. | |
| 6,786,864 | B2 | 9/2004 | Matsuura et al. | |
| 6,796,960 | B2 | 9/2004 | Cioanta et al. | |
| 6,817,976 | B2 | 11/2004 | Rovegno | |
| 6,832,715 | B2 | 12/2004 | Eungard et al. | |
| D501,677 | S | 2/2005 | Becker | |
| 6,851,290 | B1 | 2/2005 | Meier et al. | |
| 6,855,136 | B2 | 2/2005 | Dorros et al. | |
| 6,860,264 | B2 | 3/2005 | Christopher | |
| 6,860,849 | B2 | 3/2005 | Matsushita et al. | |
| 6,878,106 | B1 | 4/2005 | Herrmann | |
| 6,890,329 | B2 | 5/2005 | Carroll et al. | |
| 6,899,672 | B2 | 5/2005 | Chin et al. | |
| 6,902,556 | B2 | 6/2005 | Grimes et al. | |
| 6,927,478 | B2 | 8/2005 | Paek | |
| 6,939,361 | B1 * | 9/2005 | Kleshinski | 606/200 |
| 6,955,657 | B1 | 10/2005 | Webler | |
| 6,966,906 | B2 | 11/2005 | Brown | |
| 6,979,290 | B2 | 12/2005 | Mourlas et al. | |
| 6,984,203 | B2 | 1/2006 | Tartaglia et al. | |
| 6,991,597 | B2 | 1/2006 | Gellman et al. | |
| 6,997,931 | B2 | 2/2006 | Sauer et al. | |
| 6,997,941 | B2 | 2/2006 | Sharkey et al. | |
| 7,004,173 | B2 | 2/2006 | Sparks et al. | |
| 7,004,176 | B2 | 2/2006 | Lau | |
| 7,011,654 | B2 | 3/2006 | Dubrul et al. | |
| 7,022,105 | B1 | 4/2006 | Edwards | |
| 7,043,961 | B2 | 5/2006 | Pandey et al. | |
| 7,044,964 | B2 | 5/2006 | Jang et al. | |
| 7,052,474 | B2 | 5/2006 | Castell et al. | |
| 7,056,284 | B2 | 6/2006 | Martone et al. | |
| 7,056,303 | B2 | 6/2006 | Dennis et al. | |
| 7,074,197 | B2 | 7/2006 | Reynolds et al. | |
| 7,074,426 | B2 | 7/2006 | Kochinke | |
| 7,097,612 | B2 | 8/2006 | Bertolero et al. | |
| 7,108,706 | B2 | 9/2006 | Hogle | |
| 7,128,718 | B2 | 10/2006 | Hojeibane et al. | |
| 7,131,969 | B1 | 11/2006 | Hovda et al. | |
| 7,140,480 | B2 | 11/2006 | Drussel et al. | |
| D534,216 | S | 12/2006 | Makower et al. | |

(56) References Cited

U.S. PATENT DOCUMENTS

| | | | |
|---|---|---|---|
| 7,160,255 B2 | 1/2007 | Saadat |
| 7,169,140 B1 | 1/2007 | Kume |
| 7,169,163 B2 | 1/2007 | Becker |
| 7,172,562 B2 | 2/2007 | McKinley |
| 7,174,774 B2 | 2/2007 | Pawar et al. |
| 7,182,735 B2 | 2/2007 | Shireman et al. |
| 7,184,827 B1 | 2/2007 | Edwards |
| 7,207,981 B2 | 4/2007 | Quinn et al. |
| 7,233,820 B2 | 6/2007 | Gilboa |
| 7,235,099 B1 | 6/2007 | Duncavage et al. |
| 7,237,313 B2 | 7/2007 | Skujins et al. |
| 7,252,677 B2 | 8/2007 | Burwell et al. |
| 7,282,057 B2 | 10/2007 | Surti et al. |
| 7,292,885 B2 | 11/2007 | Scott et al. |
| 7,294,345 B2 | 11/2007 | Haapakumpu et al. |
| 7,294,365 B2 | 11/2007 | Hayakawa et al. |
| 7,303,533 B2 | 12/2007 | Johansen et al. |
| 7,316,168 B2 | 1/2008 | van der Knokke et al. |
| 7,318,831 B2 | 1/2008 | Alvarez et al. |
| 7,322,934 B2 | 1/2008 | Miyake et al. |
| 7,326,235 B2 | 2/2008 | Edwards |
| 7,338,467 B2 | 3/2008 | Lutter |
| 7,347,868 B2 | 3/2008 | Burnett et al. |
| 7,361,168 B2 | 4/2008 | Makower et al. |
| 7,366,562 B2 | 4/2008 | Dukesherer |
| 7,371,210 B2 | 5/2008 | Brock et al. |
| 7,381,205 B2 | 6/2008 | Thommen |
| 7,410,480 B2 | 8/2008 | Muni et al. |
| 7,419,497 B2 | 9/2008 | Muni et al. |
| 7,442,191 B2 | 10/2008 | Hovda et al. |
| 7,452,351 B2 * | 11/2008 | Miller et al. ............. 604/506 |
| 7,454,244 B2 | 11/2008 | Kassab et al. |
| 7,462,175 B2 | 12/2008 | Chang et al. |
| D586,465 S | 2/2009 | Faulkner et al. |
| D586,916 S | 2/2009 | Faulkner et al. |
| 7,488,313 B2 | 2/2009 | Segal et al. |
| 7,488,337 B2 | 2/2009 | Saab et al. |
| 7,493,156 B2 | 2/2009 | Manning et al. |
| 7,500,971 B2 | 3/2009 | Chang et al. |
| D590,502 S | 4/2009 | Geisser et al. |
| 7,520,876 B2 | 4/2009 | Ressemann et al. |
| 7,532,920 B1 | 5/2009 | Ainsworth et al. |
| 7,559,925 B2 | 7/2009 | Goldfarb et al. |
| 7,618,450 B2 | 11/2009 | Zarowski et al. |
| 7,625,335 B2 | 12/2009 | Deichmann et al. |
| 7,641,668 B2 | 1/2010 | Perry et al. |
| 7,645,272 B2 | 1/2010 | Chang et al. |
| 7,654,997 B2 | 2/2010 | Makower et al. |
| 7,686,798 B2 | 3/2010 | Eaton et al. |
| 7,736,301 B1 | 6/2010 | Webler et al. |
| 7,785,315 B1 | 8/2010 | Muni et al. |
| 7,799,048 B2 | 9/2010 | Hudson et al. |
| 7,799,337 B2 | 9/2010 | Levin |
| 7,837,672 B2 | 11/2010 | Intoccia |
| 7,840,254 B2 | 11/2010 | Glossop |
| D630,321 S | 1/2011 | Hamilton, Jr. |
| 7,875,050 B2 | 1/2011 | Samson et al. |
| D632,791 S | 2/2011 | Murner |
| 7,881,769 B2 | 2/2011 | Sobe |
| 7,988,705 B2 | 8/2011 | Galdonik et al. |
| 8,016,752 B2 | 9/2011 | Armstrong et al. |
| 8,104,483 B2 | 1/2012 | Taylor |
| 8,114,062 B2 | 2/2012 | Muni et al. |
| 8,146,400 B2 | 4/2012 | Goldfarb et al. |
| 8,172,828 B2 | 5/2012 | Chang et al. |
| 8,197,552 B2 | 6/2012 | Mandpe |
| 8,414,473 B2 | 4/2013 | Jenkins et al. |
| 8,425,457 B2 | 4/2013 | John et al. |
| 2001/0004644 A1 | 6/2001 | Levin |
| 2001/0005785 A1 | 6/2001 | Sachse |
| 2001/0016684 A1 | 8/2001 | Shahidi |
| 2001/0027307 A1 | 10/2001 | Dubrul et al. |
| 2001/0029317 A1 | 10/2001 | Hayakawa |
| 2001/0031941 A1 * | 10/2001 | Edwards et al. ............. 604/22 |
| 2001/0034530 A1 | 10/2001 | Malackowski et al. |
| 2001/0051761 A1 | 12/2001 | Khadem |
| 2001/0051802 A1 | 12/2001 | Woloszko et al. |
| 2002/0002349 A1 | 1/2002 | Flaherty et al. |
| 2002/0006961 A1 | 1/2002 | Katz et al. |
| 2002/0010426 A1 | 1/2002 | Clayman et al. |
| 2002/0016564 A1 | 2/2002 | Courtney et al. |
| 2002/0031941 A1 | 3/2002 | Cote et al. |
| 2002/0038130 A1 | 3/2002 | Adams |
| 2002/0055746 A1 | 5/2002 | Burke et al. |
| 2002/0062133 A1 | 5/2002 | Gilson et al. |
| 2002/0077593 A1 | 6/2002 | Perkins et al. |
| 2002/0077852 A1 | 6/2002 | Ford et al. |
| 2002/0082583 A1 | 6/2002 | Lerner |
| 2002/0090388 A1 | 7/2002 | Humes et al. |
| 2002/0107475 A1 | 8/2002 | Maginot |
| 2002/0116011 A1 | 8/2002 | Chung et al. |
| 2002/0116043 A1 | 8/2002 | Garibaldi et al. |
| 2002/0165521 A1 | 11/2002 | Cioanta et al. |
| 2003/0013985 A1 | 1/2003 | Saadat |
| 2003/0014008 A1 | 1/2003 | Jacques |
| 2003/0014036 A1 | 1/2003 | Varner et al. |
| 2003/0017111 A1 | 1/2003 | Rabito |
| 2003/0018291 A1 | 1/2003 | Hill et al. |
| 2003/0032942 A1 | 2/2003 | Theeuwes et al. |
| 2003/0040697 A1 | 2/2003 | Pass et al. |
| 2003/0069521 A1 | 4/2003 | Reynolds et al. |
| 2003/0069549 A1 | 4/2003 | MacMahon et al. |
| 2003/0073900 A1 | 4/2003 | Senarith et al. |
| 2003/0073955 A1 | 4/2003 | Otawara |
| 2003/0073972 A1 | 4/2003 | Rosenman et al. |
| 2003/0083608 A1 | 5/2003 | Evans et al. |
| 2003/0083613 A1 | 5/2003 | Schaer |
| 2003/0100886 A1 | 5/2003 | Segal et al. |
| 2003/0114732 A1 | 6/2003 | Webler et al. |
| 2003/0120339 A1 | 6/2003 | Banik et al. |
| 2003/0130598 A1 | 7/2003 | Manning et al. |
| 2003/0163154 A1 | 8/2003 | Miyata et al. |
| 2003/0164952 A1 | 9/2003 | Deichmann et al. |
| 2003/0181827 A1 | 9/2003 | Hojeibane et al. |
| 2003/0185872 A1 | 10/2003 | Kochinke |
| 2003/0208194 A1 | 11/2003 | Hovda et al. |
| 2003/0212446 A1 | 11/2003 | Kaplan et al. |
| 2003/0220551 A1 | 11/2003 | Kimball et al. |
| 2003/0225329 A1 | 12/2003 | Rossner et al. |
| 2004/0015150 A1 | 1/2004 | Zadno-Azizi |
| 2004/0018980 A1 | 1/2004 | Gurney et al. |
| 2004/0020492 A1 | 2/2004 | Dubrul et al. |
| 2004/0034311 A1 | 2/2004 | Mihalcik |
| 2004/0043052 A1 | 3/2004 | Hunter et al. |
| 2004/0058992 A1 | 3/2004 | Marinello et al. |
| 2004/0064083 A1 | 4/2004 | Becker |
| 2004/0064105 A1 | 4/2004 | Capes et al. |
| 2004/0064150 A1 | 4/2004 | Becker |
| 2004/0116958 A1 | 6/2004 | Gopferich et al. |
| 2004/0122471 A1 | 6/2004 | Toby et al. |
| 2004/0127820 A1 | 7/2004 | Clayman et al. |
| 2004/0158229 A1 | 8/2004 | Quinn |
| 2004/0167440 A1 | 8/2004 | Sharrow |
| 2004/0167442 A1 | 8/2004 | Shireman et al. |
| 2004/0167443 A1 | 8/2004 | Shireman et al. |
| 2004/0181175 A1 | 9/2004 | Clayman et al. |
| 2004/0193073 A1 | 9/2004 | DeMello et al. |
| 2004/0220516 A1 | 11/2004 | Solomon et al. |
| 2004/0230095 A1 | 11/2004 | Stefanchik et al. |
| 2004/0230131 A1 | 11/2004 | Kassab et al. |
| 2004/0230156 A1 | 11/2004 | Schreck et al. |
| 2004/0236231 A1 | 11/2004 | Knighton et al. |
| 2004/0249243 A1 | 12/2004 | Kleiner |
| 2004/0249267 A1 | 12/2004 | Gilboa |
| 2004/0254625 A1 | 12/2004 | Stephens et al. |
| 2004/0267347 A1 | 12/2004 | Cervantes |
| 2005/0027029 A1 | 2/2005 | Reifart et al. |
| 2005/0043706 A1 | 2/2005 | Eaton et al. |
| 2005/0049486 A1 | 3/2005 | Urquhart et al. |
| 2005/0055077 A1 | 3/2005 | Marco |
| 2005/0059930 A1 | 3/2005 | Garrison et al. |
| 2005/0059931 A1 | 3/2005 | Garrison et al. |
| 2005/0089670 A1 | 4/2005 | Large et al. |
| 2005/0107720 A1 | 5/2005 | Burmeister et al. |

(56) References Cited

U.S. PATENT DOCUMENTS

| | | |
|---|---|---|
| 2005/0107738 A1 | 5/2005 | Slater et al. |
| 2005/0113686 A1 | 5/2005 | Peckham |
| 2005/0113687 A1 | 5/2005 | Herweck et al. |
| 2005/0113850 A1 | 5/2005 | Tagge |
| 2005/0119590 A1 | 6/2005 | Burmeister et al. |
| 2005/0124856 A1 | 6/2005 | Fujikura et al. |
| 2005/0131316 A1 | 6/2005 | Flagle et al. |
| 2005/0143687 A1 | 6/2005 | Rosenblatt et al. |
| 2005/0182319 A1 | 8/2005 | Glossop |
| 2005/0228412 A1 | 10/2005 | Surti |
| 2005/0234507 A1 | 10/2005 | Geske et al. |
| 2005/0240147 A1 | 10/2005 | Makower et al. |
| 2005/0244472 A1 | 11/2005 | Hughes et al. |
| 2005/0245906 A1 | 11/2005 | Makower et al. |
| 2005/0273132 A1 | 12/2005 | Shluzas et al. |
| 2005/0283221 A1 | 12/2005 | Mann et al. |
| 2005/0288549 A1 | 12/2005 | Mathis |
| 2005/0288759 A1 | 12/2005 | Jones et al. |
| 2006/0004286 A1 | 1/2006 | Chang et al. |
| 2006/0004323 A1 | 1/2006 | Chang et al. |
| 2006/0047261 A1 | 3/2006 | Joshi |
| 2006/0063973 A1 | 3/2006 | Makower et al. |
| 2006/0067982 A1 | 3/2006 | Haapakumpu et al. |
| 2006/0074318 A1 | 4/2006 | Ahmed et al. |
| 2006/0085027 A1 | 4/2006 | Santin et al. |
| 2006/0095066 A1 | 5/2006 | Chang et al. |
| 2006/0106361 A1 | 5/2006 | Muni et al. |
| 2006/0107957 A1 | 5/2006 | Djupesland |
| 2006/0116749 A1 | 6/2006 | Willink et al. |
| 2006/0149310 A1 | 7/2006 | Becker |
| 2006/0161255 A1 | 7/2006 | Zarowski et al. |
| 2006/0173382 A1 | 8/2006 | Schreiner |
| 2006/0189844 A1 | 8/2006 | Tien |
| 2006/0190022 A1 | 8/2006 | Beyar et al. |
| 2006/0210605 A1 | 9/2006 | Chang et al. |
| 2006/0211752 A1 | 9/2006 | Kohn et al. |
| 2006/0271024 A1 | 11/2006 | Gertner et al. |
| 2007/0005094 A1 | 1/2007 | Eaton et al. |
| 2007/0020196 A1 | 1/2007 | Pipkin et al. |
| 2007/0049929 A1 | 3/2007 | Catanese, III et al. |
| 2007/0073269 A1 | 3/2007 | Becker |
| 2007/0112358 A1 | 5/2007 | Abbott et al. |
| 2007/0129751 A1 | 6/2007 | Muni et al. |
| 2007/0135789 A1 | 6/2007 | Chang et al. |
| 2007/0167682 A1 | 7/2007 | Goldfarb et al. |
| 2007/0207186 A1 | 9/2007 | Scanlon et al. |
| 2007/0208252 A1 | 9/2007 | Makower |
| 2007/0208301 A1 | 9/2007 | Evard et al. |
| 2007/0233036 A1 | 10/2007 | Mandpe |
| 2007/0250105 A1 | 10/2007 | Ressemann et al. |
| 2007/0269385 A1 | 11/2007 | Yun et al. |
| 2007/0293727 A1 | 12/2007 | Goldfarb et al. |
| 2007/0293946 A1 | 12/2007 | Gonzales et al. |
| 2008/0015540 A1 | 1/2008 | Muni et al. |
| 2008/0015544 A1 | 1/2008 | Keith et al. |
| 2008/0033519 A1 | 2/2008 | Burwell et al. |
| 2008/0051804 A1 | 2/2008 | Cottler et al. |
| 2008/0082045 A1 | 4/2008 | Goldfarb et al. |
| 2008/0097154 A1 | 4/2008 | Makower et al. |
| 2008/0097239 A1 | 4/2008 | Chang et al. |
| 2008/0097295 A1 | 4/2008 | Makower et al. |
| 2008/0097400 A1 | 4/2008 | Chang et al. |
| 2008/0097514 A1 | 4/2008 | Chang et al. |
| 2008/0097515 A1 | 4/2008 | Chang et al. |
| 2008/0097516 A1 | 4/2008 | Chang et al. |
| 2008/0103361 A1 | 5/2008 | Makower et al. |
| 2008/0103521 A1 | 5/2008 | Makower et al. |
| 2008/0119693 A1 | 5/2008 | Makower et al. |
| 2008/0125046 A1 | 5/2008 | Deng et al. |
| 2008/0125626 A1 | 5/2008 | Chang et al. |
| 2008/0154250 A1 | 6/2008 | Makower et al. |
| 2008/0172033 A1 | 7/2008 | Keith et al. |
| 2008/0187098 A1 | 8/2008 | Gertner et al. |
| 2008/0188870 A1 | 8/2008 | Andre et al. |
| 2008/0195041 A1 | 8/2008 | Goldfarb et al. |
| 2008/0208242 A1 | 8/2008 | Becker |
| 2008/0208243 A1 | 8/2008 | Becker |
| 2008/0215082 A1 | 9/2008 | Becker |
| 2008/0215083 A1 | 9/2008 | Becker |
| 2008/0228085 A1 | 9/2008 | Jenkins et al. |
| 2008/0234720 A1 | 9/2008 | Chang et al. |
| 2008/0262508 A1 | 10/2008 | Clifford et al. |
| 2008/0262509 A1 | 10/2008 | Clifford et al. |
| 2008/0275483 A1 | 11/2008 | Makower et al. |
| 2008/0281156 A1 | 11/2008 | Makower et al. |
| 2008/0287908 A1 | 11/2008 | Muni et al. |
| 2008/0319424 A1 | 12/2008 | Muni et al. |
| 2009/0017090 A1 | 1/2009 | Arensdorf et al. |
| 2009/0028923 A1 | 1/2009 | Muni et al. |
| 2009/0030274 A1 | 1/2009 | Goldfarb et al. |
| 2009/0047326 A1 | 2/2009 | Eaton et al. |
| 2009/0088677 A1 | 4/2009 | Cohen |
| 2009/0088728 A1 | 4/2009 | Dollar et al. |
| 2009/0093823 A1 | 4/2009 | Chang et al. |
| 2009/0156980 A1 | 6/2009 | Eaton et al. |
| 2009/0187089 A1 | 7/2009 | Say et al. |
| 2009/0187098 A1 | 7/2009 | Makower et al. |
| 2009/0227945 A1 | 9/2009 | Eaton et al. |
| 2009/0240112 A1 | 9/2009 | Goldfarb et al. |
| 2009/0240237 A1 | 9/2009 | Goldfarb et al. |
| 2009/0312745 A1 | 12/2009 | Goldfarb et al. |
| 2010/0042046 A1 | 2/2010 | Chang et al. |
| 2010/0087811 A1 | 4/2010 | Herrin et al. |
| 2010/0114066 A1 | 5/2010 | Makower et al. |
| 2010/0174138 A1 | 7/2010 | Chang et al. |
| 2010/0174308 A1 | 7/2010 | Chang et al. |
| 2010/0174366 A1 | 7/2010 | Avior |
| 2010/0198191 A1 | 8/2010 | Clifford et al. |
| 2010/0198247 A1 | 8/2010 | Chang et al. |
| 2010/0198302 A1 | 8/2010 | Shalev |
| 2010/0210901 A1 | 8/2010 | Makower et al. |
| 2010/0268245 A1 | 10/2010 | Chang et al. |
| 2010/0274188 A1 | 10/2010 | Chang et al. |
| 2010/0290244 A1 | 11/2010 | Nath |
| 2010/0298862 A1 | 11/2010 | Chang et al. |
| 2011/0004057 A1 | 1/2011 | Goldfarb et al. |
| 2011/0015482 A1 | 1/2011 | Carrillo, Jr. |
| 2011/0060214 A1 | 3/2011 | Makower |
| 2011/0112512 A1 | 5/2011 | Muni et al. |
| 2011/0166190 A1 | 7/2011 | Anderson et al. |
| 2012/0071710 A1 | 3/2012 | Gazdzinski |
| 2012/0071824 A1 | 3/2012 | Chang et al. |
| 2012/0136207 A1 | 5/2012 | Goldfarb et al. |
| 2012/0184983 A1 | 7/2012 | Chang et al. |
| 2012/0245419 A1 | 9/2012 | Makower et al. |
| 2012/0265094 A1 | 10/2012 | Goldfarb et al. |
| 2013/0231529 A1 | 9/2013 | Chang et al. |
| 2013/0245608 A1 | 9/2013 | Muni et al. |
| 2013/0261388 A1 | 10/2013 | Jenkins et al. |

FOREIGN PATENT DOCUMENTS

| | | |
|---|---|---|
| CN | 2151720 | 1/1994 |
| CN | 2352818 | 12/1999 |
| DE | 3202878 | 8/1983 |
| DE | 8810044 | 12/1988 |
| DE | 4032096 | 4/1992 |
| DE | 4406077 | 9/1994 |
| DE | 29923582 | 12/2000 |
| DE | 10104663 | 8/2002 |
| DE | 10105592 | 8/2002 |
| EP | 129634 | 1/1985 |
| EP | 0200430 | 11/1986 |
| EP | 0257605 | 3/1988 |
| EP | 355996 | 2/1990 |
| EP | 418391 | 3/1991 |
| EP | 427852 | 5/1991 |
| EP | 0515201 | 11/1992 |
| EP | 623582 | 11/1994 |
| EP | 624349 | 11/1994 |
| EP | 744400 | 11/1996 |
| EP | 585757 | 6/1997 |
| EP | 893426 | 1/1999 |
| EP | 0920882 | 6/1999 |

(56) References Cited

FOREIGN PATENT DOCUMENTS

| | | |
|---|---|---|
| EP | 0974936 | 1/2000 |
| EP | 1042998 | 10/2000 |
| EP | 1086664 | 3/2001 |
| EP | 1166710 | 1/2002 |
| EP | 1413258 | 4/2004 |
| EP | 1944053 | 7/2008 |
| FR | 2859377 | 3/2005 |
| FR | 2916144 | 11/2008 |
| GB | 2125874 | 3/1984 |
| GB | 2305174 | 4/1997 |
| JP | 5367935 | 6/1978 |
| JP | 10-24098 | 1/1989 |
| JP | 3-503011 | 7/1991 |
| JP | 3-504935 | 10/1991 |
| JP | 4-221313 | 8/1992 |
| JP | 4-224766 | 8/1992 |
| JP | 5-503650 | 6/1993 |
| JP | 5-211985 | 8/1993 |
| JP | 6-277296 | 10/1994 |
| JP | 07-327916 | 12/1995 |
| JP | 7-327916 | 12/1995 |
| JP | 8-317989 | 12/1996 |
| JP | 11-507251 | 6/1999 |
| JP | 2000-501634 | 2/2000 |
| JP | 2001-501846 | 2/2001 |
| JP | 2001-095815 | 4/2001 |
| JP | 2001-526077 | 12/2001 |
| JP | 2002-028166 | 1/2002 |
| JP | 2002-508214 | 3/2002 |
| JP | 2002-537908 | 11/2002 |
| JP | 2002-538850 | 11/2002 |
| JP | 2003-507140 | 2/2003 |
| JP | 2003-062080 | 3/2003 |
| JP | 2003-521327 | 7/2003 |
| JP | 2004-357728 | 12/2004 |
| JP | 2005-532869 | 11/2005 |
| RU | 2213530 | 10/2003 |
| SU | 1662571 | 7/1991 |
| WO | WO 90/11053 | 10/1990 |
| WO | WO 90/14865 | 12/1990 |
| WO | WO 91/17787 | 11/1991 |
| WO | WO 92/15286 | 9/1992 |
| WO | WO 92/22350 | 12/1992 |
| WO | WO 94/12095 | 6/1994 |
| WO | WO 94/21320 | 9/1994 |
| WO | WO 95/02430 | 1/1995 |
| WO | WO 96/29071 | 9/1996 |
| WO | WO 97/21461 | 6/1997 |
| WO | WO 98/55174 | 12/1998 |
| WO | WO 99/00064 | 1/1999 |
| WO | WO 99/24106 | 5/1999 |
| WO | WO 99/26692 | 6/1999 |
| WO | WO 99/30655 | 6/1999 |
| WO | WO 99/32041 | 7/1999 |
| WO | WO 99/59649 | 11/1999 |
| WO | WO 00/09190 | 2/2000 |
| WO | WO 00/09192 | 2/2000 |
| WO | WO 00/23009 | 4/2000 |
| WO | WO 00/51672 | 9/2000 |
| WO | WO 00/53252 | 9/2000 |
| WO | WO 01/05462 | 1/2001 |
| WO | WO 01/45572 | 6/2001 |
| WO | WO 01/54558 | 8/2001 |
| WO | WO 01/56481 | 8/2001 |
| WO | WO 01/70325 | 9/2001 |
| WO | WO 01/74266 | 10/2001 |
| WO | WO 01/97895 | 12/2001 |
| WO | WO 02/062269 | 8/2002 |
| WO | WO 02/089899 | 11/2002 |
| WO | WO 03/049603 | 6/2003 |
| WO | WO 03/063703 | 8/2003 |
| WO | WO 03/105657 | 12/2003 |
| WO | WO 2004/006788 | 1/2004 |
| WO | WO 2004/018980 | 3/2004 |
| WO | WO 2004/026391 | 4/2004 |
| WO | WO 2004/082525 A2 | 9/2004 |
| WO | WO 2004/082525 A3 | 9/2004 |
| WO | WO 2005/018730 | 3/2005 |
| WO | WO 2005/077450 | 8/2005 |
| WO | WO 2005/089670 | 9/2005 |
| WO | WO 2005/117755 | 12/2005 |
| WO | WO 2006/034008 | 3/2006 |
| WO | WO 2006/078884 | 7/2006 |
| WO | WO 2006/107957 | 10/2006 |
| WO | WO 2006/116597 | 11/2006 |
| WO | WO 2006/118737 | 11/2006 |
| WO | WO 2006/135853 | 12/2006 |
| WO | WO 2007/035204 | 3/2007 |
| WO | WO 2007/111636 | 10/2007 |
| WO | WO 2007/124260 | 11/2007 |
| WO | WO 2008/036149 | 3/2008 |
| WO | WO 2008/045242 | 4/2008 |
| WO | WO 2008/051918 | 5/2008 |
| WO | WO 2008/134382 | 11/2008 |

OTHER PUBLICATIONS

Göttman, et al., Balloon dilatation of recurrent ostial occlusion of the front sinus; ECR, Mar. 2, 2001.
Göttman, et al., Successful Treatment of Recurrent Post-operative Frontal Sinus Stenoses by Balloon Dilatation; CIRSE, Oct. 5, 2002.
Göttman, et al., Balloon dilatation in the nasal cavity and paranasal sinuses; CIRSE, Sep. 25, 2004.
Robison, J. Mathews, M.D., Pressure Treatment of Purulent Maxillary Sinusitis, Texas State Journal of Medicine, May 1951, pp. 281-288.
Robison, J. Mathews, M.D., Pressure Treatment of Maxillary Sinusitis, J.A.M.A., May 31, 1952, pp. 436-440.
Strohm et al. Die Behandlung von Stenosen der oberen Luftwege mittels rontgenologisch gesteuerter Ballondilation Sep. 25, 1999.
USPTO Office Action dated Oct. 29, 2008 in U.S. Appl. No. 11/347,147, filed Feb. 2, 2006.
USPTO Office Action dated Mar. 3, 2009 in U.S. Appl. No. 12/117,582, filed May 8, 2008.
USPTO Office Action dated Nov. 25, 2008 in U.S. Appl. No. 12/117,961, filed May 9, 2008.
USPTO Office Action dated Mar. 4, 2009 in U.S. Appl. No. 12/118,931, filed May 12, 2008.
USPTO Office Action dated Dec. 5, 2008 in U.S. Appl. No. 12/120,902, filed May 15, 2008.
USPTO Office Action dated Oct. 6, 2008 in U.S. Appl. No. 10/259,300, filed Sep. 30, 2002.
USPTO Office Action dated Oct. 9, 2007 in U.S. Appl. No. 10/259,300, filed Sep. 30, 2002.
USPTO Office Action dated Jul. 7, 2006 in U.S. Appl. No. 10/259,300, filed Sep. 30, 2002.
USPTO Office Action dated Jan. 24, 2008 in U.S. Appl. No. 10/259,300, filed Sep. 30, 2002.
USPTO Office Action dated Feb. 13, 2007 in U.S. Appl. No. 10/259,300, filed Sep. 30, 2002.
USPTO Office Action dated Mar. 17, 2009 in U.S. Appl. No. 11/690,127, filed Mar. 22, 2007.
http://www.invotec.net/rhinology/ksplint.html. K-Splint Internal Nasal Splints; Jan. 25, 2007.
http://www.doylemedical.com/nasalsplints.htm; Doyle Nasal Splints; Jan. 25, 2007.
http://www.technologyforlife.com.au/ent/nasal.html; Nasal Surgery and Accessories; Jan. 25, 2007.
Barrett, S. 'Be Wary of Neurocranial Restructuring (NCR)' Chirobase (available at: http://www.chirobase.org/06DD/ncr.html) (Jul. 2003.).
Bartal, N. 'An Improved Stent for Use in the Surgical Management of Congenital Posterior Choanal Atresia' J. Laryngol. Otol (1988) vol. 102 pp. 146-147.
Benninger et al.; Adult Chronic Rhinosinusitis: Definitions, Diagnosis, Epidemiology, and Pathophysiology' Arch Otolaryngol Head and Neck Surg. vol. 129 (Sep. 2003) pp. S1-S32.
Bent et al. 'The Frontal Cell as a Cause of Frontal Sinus Obstruction' American Journal of Rhinology. vol. 8, No. 4 (1994) pp. 185-191.

(56) References Cited

OTHER PUBLICATIONS

Binner et al. 'Fibre-Optic Transillumination of the Sinuses: A Comparison of the Value of Radiography and Transillumination in Antral Disease' Clinical Otolaryngology. vol. 3 (1978) pp. 1-11.
Bumm, P., H. Kaiser et al 'Cortizontherapie, Corticoide in Klinik and Praxis' Thieme, Stuggart (1992) pp. 390-401.
Casiano et al. 'Endoscopic Lothrop Procedure: The University of Miami Experience' American Journal of Rhinology. vol. 12, No. 5 (1998) pp. 335-339.
Chien, Y.W. et al. 'Nasal Systemic Drug Delivery, Drugs and the Pharmaceutical Sciences' vol. 39, pp. 60-63.
Cohen et al 'Endoscopic Sinus Surgery: Where we are and where we're going' Current Opinion in Otolaryngology & Head and Neck Surgery. vol. 13 (2005) pp. 32-38.
Colla, A. et al 'Trihaloacetylated Enol Ethers-General Synthetic Procedure and Heterocyclic Ring Closure Reactions with Hydroxylamine' Synthesis. (Jun. 1991) pp. 483-486.
Costa, M.N. et al 'Endoscopic Study of the Intranasal Ostium in External Dacryocystorhinostomy Postoperative. Influence of Saline Solution and 5-Flurorouracil' Clinics. (2007) vol. 62, Issue 1 pp. 41-46. http://www.scielo.br/scielo.php?pid=S1807-59322007000100007&script=sci_arttext.
Cox, Laryngoscope. (1986) vol. 96. pp. 579 Came in as Fung Article.
Croix, et al. 'Genes Expressed in Human Tumor Endothelium' Science. vol. 289 (May 15, 2000) pp. 1197-1202.
Cussler, E.L. 'Diffusion: Mass Transfer in Fluid Systems' Cambridge University Press (1996).
Davis, G.E. et al., 'A Complication From Neurocranial Restructuring' Arch Otolaryngol Head Neck Surg. vol. 129 (Apr. 2003) pp. 472-474.
Deutschmann, R. et al. 'A Contribution to the Topical Treatment of [Maxillary] Sinusitis Preliminary Communication' Stomat DDR 26, (1976) pp. 585-592.
Domb, A. et al 'Handbook of Biodegradable Polymers' Harwood Academic Publishers (1997).
Draf, W. 'Endonasal Micro-Endoscopic Frontal Sinus Surgery: the Fulda Concept' Op Tech Otolaryngol Head Neck Surg. vol. 2 (1991) pp. 234-240.
Edmond, C. et al 'ENT Surgical Stimulator' Nov. 1989.
Eremychev, V.A. 'Needles for Puncture and Drainage of the Maxillary Sinus' Meditsinskaya Tekhnika, No. 5 (1974) pp. 54-55.
Friedman, M. M.D., et al 'Frontal Sinus Surgery: Endoscopic Technique' Operative Techniques in Otolarynology-Head and Neck Surgery. vol. 12, No. 2 (Jun. 2001) pp. 60-65.
Friedman, et al 'Intraoperative and Postoperative Assessment of Frontal Sinus Patency by Transillumination' Laryngoscope. vol. 110 (Apr. 2000) pp. 683-684.
Friedman et al 'Middle Turbinate Medialization and Preservation in Endoscopic Surgery' Otolaryngology-Head and Neck Surgery. (2000) vol. 123, No. 1, Part 1. pp. 76-80.
Fung, M.K.T. 'How I Do It—Head and Neck and Plasic Surgery. A Targeted Problem and its Solution. Template for Frontal Osteoplastic Flap' Laryngoscope. vol. 96 (1986) pp. 578-579.
Gatot, A. et al., 'Early Treatment of Orbital Floor Fractures with Catheter Balloon in Children' Int J Pediatric Otorhinolaryngol (1991) vol. 21 pp. 97-101.
Gerus, I.I. et al 'β-Ethoxyvinyl Polyfluroroalkyl Ketones-Versatile Synthones in Fluoroorganic Chemistry' Journal of Fluorine Chemistry. vol. 69 (1994) pp. 195-198. Elsevier Science S.A.
Good, R.H. 'An Intranasal Method for Opening the Frontal Sinus Establishing the Largest Possible Drainage' Laryngoscope. vol. 18, (1908) pp. 266-274.
Gopferich 'Polymer Degradation and Erosion: Mechanisms and Applications' Eur. J. Pharm. Biophar. vol. 42 (1996) pp. 1-11.
Gorlov, D.V. et al 'Acylation of 2-Methoxypropene with Anhydrides and Halides of Perflurocarboxylic Acids in the Presence of Tertiary Amines' Russian Chemical Bulletin. vol. 48 No. 9 (Sep. 1999) pp. 1791-1792. Kluwer Academic/Plenurn Publishers.
Gottman, et al. 'Balloon Dilatation in the Nasal Cavity and Paranasal Sinuses' CIRSE. (Sep. 25, 2004) pp. 1-27.
Gottman, et al. 'Balloon Dilatation of Recurrent Ostial Occlusion of the Front Sinus' No. B-0453. European Congress of Radiology. (Mar. 2, 2001) pp. 194.
Gottman, et al. 'Successful Treatment of Recurrent Post-Operative Frontal Sinus Stenoses by Balloon Dilatation' CIRSE. (Oct. 5, 2002).
Gottmann, D. 'Treatment of Stenoses of Upper Air Routes by Balloon Dilation' Proceeding of the 83rd Annual Convention of the Association of West German ENT Physicians (1999).
Hashim, et al 'Balloon Compression of the Intermaxillary Sinus for Intractable Post Traumatic Bleeding from the Maxillary Artery' Scandinavian Journal of Plastic and Reconstructive Surgery and Hand Surgery (1999) vol. 33 pp. 321-324.
Hojo, M. et al 'Electrophilic Substitutions of Olefinic Hydrogens II. Acylation of Vinyl Ethers and N Vinyl Amides Chemistry Letters' (1976) pp. 499-502. Chemical Society of Japan.
Hosemann, W. et al 'Endonasal Frontal Sinusotomy in Surgical Management of Chronic Sinusitis: A Critical Evaluation' American Journal of Rhinology. vol. 11, No. 1 (1997) pp. 1-9.
Hosemann, M.E. et al 'Experimentelle Untersuchungen zur Wundheilung in den Nasennebenholhlen. II. Spontaner Wundschluss and medikamentose Effekte im standardisierten Wundmodell.' HNO 39 (1991) pp. 48-54.
Hosemann W.G. et al 'Minimally Invasive Endonasal Sinus Surgery' Thieme, Stuttgart, New York (2000).
Hosemann, M.E. et al 'Normal Wound Healing of the Paranasal Sinuses—Clinical and Experimental Investigations' Eur Arch Otorhinolaryngol. vol. 248, (1991) pp. 390-394.
Hosemann, W. et al 'Weiterbehandlung nach Nasennebenhohleneingriffen, Part 2: Theapeutische Maβnahmen' HNO akutell 7 (1999) pp. 291-302.
Hospital Corpsman Sickcall Screener's Handbook. Naval Hospital Great Lakes (Apr. 1999) http://www.brooksidepress.org/Products/Operationa.Medicine/DATA. 2001 pp. 1-6.
Hybels, R.L. 'Transillumination During Osteoplastic Frontal Sinusotomy' The Laryngoscope. vol. 91 (Sep. 1981) pp. 1560.
Ijaduola, T.G.A. 'Use of a Foley Catheter for Short-Term Drainage in Frontal Sinus Surgery' The Journal of Laryngology and Otology. (1989) vol. 103. pp. 375-378.
Ingals, E.F. 'New Operation and Instruments for Draining the Frontal Sinus' Ann. Otol Rhinol Laryngol. vol. 14 (1905) pp. 644-649.
Jacobs, J.B. '100 Years of Frontal Sinus Surgery' Laryngoscope. vol. 107 (1997) pp. 1-36.
Kennedy, D.W., M.D. et al 'Diseases of the Sinuses Diagnosis and Management' (Copyright 2001) by B.C. Decker Inc.
Khomutov, S.M. et al 'Dissolution of a Mixture of Steroids in Cyclodextrin Solutions: a Model Description' Pharmaceutical Chemistry Journal. vol. 35, No. 11 (Nov. 2001) pp. 627-629.
Kingdom, T.T. et al 'Image-Guided Surgery of the Sinuses: Current Technology and Applications' Otolaryngol. Clin. North Am. vol. 37, No. 2 (Apr. 2004) pp. 381-400.
Klossek, J.M. et al 'Local Safety of Intranasal Triamcinolone Acetonide: Clinical and Histological Aspects of Nasal Mucosa in the Long-Term Treatment of Perennial Allergic Rhinitis' Rhinology. vol. 39, No. 1 (2001) pp. 17-22.
Kozlov et al 'Diagnosis and Treatment of Sinusitis by YAMIK Sinus Catheters' Rhinology (1996) vol. 34. pp. 123-124.
Kuhn, et al. 'The Agger Nasi Cell in Frontal Recess Obstruction: An Anatomic, Radiology and Clinical Correlation' Operative Techniques in Otolaryngology-Head and Neck Surgery. vol. 2, No. 4 (1991) pp. 226-231.
Laliberte F. et al 'Clinical and Pathologic Methods to Assess the Long-Term Safety or Nasal Corticosteroids' Allergy. vol. 55, No. 8 (2000) pp. 718-722.
Lanza, D.C. 'Postoperative Care and Avoiding Frontal Recess Stenosis, International Advanced Sinus Symposium' (1993) Jul. 21-24.
Lund, V.J. 'Maximal Medical Therapy for Chronic Rhinosinusitis' Otolaryngol Clin N Am. vol. 38 (2005) pp. 1301-1310.
Maran, A.G.D. et al 'The Use of the Foley Catheter in the Tripod Fracture' J. Laryngol Otol (1971) vol. 85, Issue 9. pp. 897-902.
May, M. et al 'Frontal Sinus Surgery: Endonasal Drainage Instead of an External Osteopolstic Approach' Op Tech Otolaryngo Head Neck Surgery. 6 (1995) pp. 184-192.

(56) References Cited

OTHER PUBLICATIONS

Medtronic, xomed.com—MicroFrance Catalog Browser. http://www.xomcat.com/xomfrance/index.php?zone=both&cat=18&sub=58&prodline=1272 (Dec. 31, 2003) pp. 1-2.
Mellor, J.M. et al 'Synthesis of Trifluromethylnaphthalenes' Tetrahedron. vol. 56 (2000) pp. 10067-10074. Elseview Science Ltd.
Metson, R. 'Holmium: YAG Laser Endoscopic Sinus Surgery: A Randomized Controlled Study' Laryngoscope. vol. 106, Issue 1, Supplement 77 (Jan. 1996) pp. 1-18.
Miller et al. 'Management of Fractures of the Supraorbital Rim' Journal of Trauma. vol. 18, No. 7 (Jul. 1978) pp. 507-512.
Min, Y-G et al. 'Mucociliary Activity and Histopathology of Sinus Mucosa in Experimental Maxilary Sinusitis: A Comparison of Systemic Administration of Antibiotic and Antibiotic Delivery by Polylactic Acid Polymer' Laryngoscope. vol. 105 (Aug. 1995) pp. 835-842.
Mols, B. 'Moveable Tool Tip for Keyhole Surgery' Delft Outlook, vol. 3 (2005) pp. 13-17.
Moriguchi, T. et al 'Addition-Elimination Reaction in the Trifluoroacetylation of Electron-Rich Olefins' J. Org. Chem. vol. 60, No. 11 (1995) pp. 3523-3528. American Chemical Society.
Park, K. et al 'Biogreadable Hydrogels for Medicinal Substance Delivery' (1993) Technomic Publishing Inc. Lancaster.
Piccirillo, J.F. et al 'Psychometric and Clinimetric Validity of the 20-Item Sino-Nasal Outcome Test (SNOT-20)' Copyright© 1996 Washington University, St. Louis, Missouri.
Piers, et al 'A Flexible Distal Tip with Two Degrees of Freedom for Enhanced Dexterity in Endoscopic Robot Surgery' Proceedings 13th Micromechanics Europe Workshop (2002) pp. 271-274.
Podoshin, L. et al 'Balloon Technique for Treatment of Frontal Sinus Fractures' The Journal of Laryngology & Otology (1967), vol. 81. pp. 1157-1161.
Prince et al 'Analysis of the Intranasal Distribution of Ointment' J Otolaryngol. vol. 26 (1997) pp. 357-360.
Robison, J. Mathews, M.D. 'Pressure Treatment of Maxillary Sinusitis' J.A.M.A. (May 31, 1952) pp. 436-440.
Robison, J. Mathews, M.D. 'Pressure Treatment of Purulent Maxillary Sinusitis' Texas State Journal of Medicine. (May 1951) pp. 281-288.
Sawbones Catalog 2001, Pacific Research Laboratories, Inc., Vashon, Washington 98070 USA.
Schaefer, S.D., M.D. 'Rhinology and Sinus Disease a Problem-Oriented Approach' (Copyright 1988) by Mosby, Inc.
Shah, N.J. 'Functional Endoscopic Sinus Surgery' (1999); found at www.bhj.org/journal/1999_4104_oct99/sp_659.htm.
Single-Pole and Multi-Pole Lightguides for UV Spot Light Curing Systems. http://www.dymax.com/products/curing_equipment/lightguids/light. (2004) pp. 1-2.
Sobol, et al 'Sinusitis, Maxillary, Acute Surgical Treatment.' eMedicine. Retrieved from the Internet: <<http://emedicine.medscape.com/article/862030-print>> (Nov. 16, 2010) pp. 1-11.
Stammberger H. 'Komplikationen entzundlicher Nasen-nebenhohlenerkrankungen eischließlich iatrogen bedingter Komplikationen.' Eur Arch Oti-Rhino-Laryngol Suppl. (Jan. 1993) pp. 61-102.
Stammberger, et al 'Special Endoscopic Anatomy of the Lateral Nasal Wall and Ethmoidal Sinuses' Functional Endoscopic Sinus Surgery. (1991) Ch. 3, pp. 49-87.
Strohm et al Die Behandlung von Stenosen der oberen Luftwege mittels rontgenologisch gesteuerter Ballondilation (Sep. 25, 1999) pp. 1-4.
Strohm, et al 'Treatment of the Stenoses of the Upper Air Routes by Balloon Dilation' Sudwestdeutscher Abstract 45 (Sep. 25, 1999) pp. 1-3.
SurgTrainer Product Information 2003, Surg Trainer, Ltd. Ibaraki, Japan.
Tarasov, D.I. et al. 'Application of Drugs Based on Polymers in the Treatment of Acute and Chronic Maxillary Sinusitis' Vestn Otorinolaringol. vol. 6 (1978) pp. 45-47.

The Operating Theatre Journal (www.otjonline.com) 'Disposable Medical Device for Wound Disclosure/The Tristel Purple Promotion—A Collaboration between Tristel plc and Karl Storz Endoscopy (UK) Ltd.' pp. 4.
Weber, R. et al 'Endonasale Stirnhohlenchirugie mit Langzeiteinlage eines Platzhalters' Laryngol. Rhinol Otol. vol. 76 (1997) pp. 728-734. (English Abstract).
Weber, R. et al 'Videoendoscopic Analysis of Nasal Steroid Distribution' Rhinology. vol. 37 (1999) pp. 69-73.
Woog, et al. 'Paranasal Sinus Endoscopy and Orbital Fracture Repair' Arch Ophthalmol. vol. 116 (May 1998) pp. 688-691.
Yamauchi, Y. et al 'Development of a Silicone Model for Endoscopic Sinus Surgery' proc International Journal of Computer Assisted Radiology and Surgery vol. 99 (1999) pp. 1039.
Yanagisawa et al 'Anterior and Posterior Fontanelles.' Ear, Nose & Throat Journal (2001) vol. 80. p. 10-12.
EP Communication dated Sep. 4, 2008 re: EP 05773189.
EP Communication dated Jun. 19, 2009 re: EP 05773189.
Examiners First Report dated Apr. 8, 2010 re: AU2005274794.
Examination Report dated Feb. 22, 2006 re: 02716734.5.
Examination Report dated Feb. 8, 2007 re: 02716734.5.
European Search Report and Search Opinion dated Sep. 11, 2009 from EP06815174.
European Search Report dated Mar. 16, 2010 from EP06718986.
International Preliminary Report on Patentability dated Aug. 25, 2006 from PCT/US05/25371.
International Preliminary Report on Patentability dated Oct. 4, 2007 from PCT/US06/002004.
International Preliminary Report dated Feb. 15, 2008 from PCT/US05/13617.
International Preliminary Report on Patentability dated Nov. 27, 2008 from PCT/US07/11449.
International Preliminary Report on Patentability dated Apr. 16, 2009 from PCT/US07/021170.
International Preliminary Report on Patentability dated May 14, 2009 from PCT/US06/36960.
International Preliminary Report on Patentability dated Oct. 22, 2009 from PCT/US08/059786.
International Preliminary Report on Patentability dated Nov. 5, 2009 from PCT/US08/061343.
International Search Report dated May 23, 2002 from PCT/EP02/01228.
International Search Report and Written Opinion dated Apr. 10, 2006 from PCT/US05/25371.
International Search Report and Written Opinion dated Aug. 17, 2007 from PCT/US05/13617.
International Search Report and Written Opinion dated Aug. 29, 2007 from PCT/US06/002004.
International Search Report and Written Opinion dated May 29, 2008 from PCT/US07/021170.
International Search Report dated May 28, 2008 from PCT/US07/21922.
International Search Report and Written Opinion dated Jul. 1, 2008 from PCT/US06/22745.
International Search Report dated Jul. 7, 2008 from PCT/US07/16213.
International Search Report and Written Opinion dated Jul. 17, 2008 from PCT/US06/36960.
International Search Report and Written Opinion dated Jul. 21, 2008 from PCT/US05/33090.
International Search Report dated Aug. 25, 2008 from PCT/US2008/000911.
International Search Report and Written Opinion dated Sep. 12, 2008 from PCT/US07/16214.
International Search Report and Written Opinion dated Sep. 17, 2008 from PCT/US08/059786.
International Search Report and Written Opinion dated Sep. 27, 2008 from PCT/US08/061343.
International Search Report and Written Opinion dated Oct. 1, 2008 from PCT/US07/11449.
Supplemental European Search Report dated Jun. 2, 2008 re: EP05773189.

(56) References Cited

OTHER PUBLICATIONS

International Search Report dated Dec. 10, 2009 re: PCT/US2009/052236.
International Search Report dated Dec. 16, 2009 re: PCT/US2009/050800.
Supplemental European Search Report dated Feb. 2, 2010 re: EP07836109.
Supplemental European Search Report dated Feb. 17, 2010 re: EP07836110.
Supplemental European Search Report dated Mar. 22, 2010 re: EP05778834.
Supplemental European Search Report dated Jun. 22, 2010 re: EP06784759.
Supplemental Partial European Search Report dated Nov. 19, 2010 re: EP06751637.
PCT Search Report from PCT Application No. PCT/US2009/057203 dated Nov. 30, 2009 as issued by the European Patent Office as searching authority.
U.S. Appl. No. 10/259,300.
U.S. Appl. No. 10/259,630.
U.S. Appl. No. 10/829,917.
U.S. Appl. No. 10/912,578.
U.S. Appl. No. 10/944,270.
U.S. Appl. No. 11/037,548.
U.S. Appl. No. 11/116,118.
U.S. Appl. No. 11/150,847.
U.S. Appl. No. 11/150,874.
U.S. Appl. No. 11/193,020.
U.S. Appl. No. 11/234,395.
U.S. Appl. No. 11/347,147.
U.S. Appl. No. 11/355,512.
U.S. Appl. No. 11/436,892.
U.S. Appl. No. 11/436,897.
U.S. Appl. No. 11/438,090.
U.S. Appl. No. 11/522,497.
U.S. Appl. No. 11/527,773.
U.S. Appl. No. 11/544,009.
U.S. Appl. No. 11/647,530.
U.S. Appl. No. 11/648,159.
U.S. Appl. No. 11/655,794.
U.S. Appl. No. 11/725,151.
U.S. Appl. No. 11/789,704.
U.S. Appl. No. 11/789,705.
U.S. Appl. No. 11/803,695.
U.S. Appl. No. 11/925,540.
U.S. Appl. No. 11/926,326.
U.S. Appl. No. 11/926,565.
U.S. Appl. No. 11/928,097.
U.S. Appl. No. 12/011,100.
U.S. Appl. No. 12/100,361.
U.S. Appl. No. 12/117,582.
U.S. Appl. No. 12/117,672.
U.S. Appl. No. 12/117,961.
U.S. Appl. No. 12/118,931.
U.S. Appl. No. 12/120,902.
U.S. Appl. No. 12/122,884.
U.S. Appl. No. 12/340,226.
U.S. Appl. No. 12/341,602.
U.S. Appl. No. 12/502,101.
U.S. Appl. No. 60/844,874.
U.S. Appl. No. 60/922,730.
U.S. Appl. No. 61/052,413.
U.S. Appl. No. 61/084,949.
USPTO Office Action dated Sep. 16, 2005 in U.S. Appl. No. 10/259,300.
USPTO Office Action dated Jul. 7, 2006 in U.S. Appl. No. 10/259,300.
USPTO Office Action dated Feb. 13, 2007 in U.S. Appl. No. 10/259,300.
USPTO Office Action dated May 29, 2007 in U.S. Appl. No. 10/912,578.
USPTO Office Action dated Oct. 9, 2007 in U.S. Appl. No. 10/259,300.
USPTO Office Action dated Oct. 18, 2007 in U.S. Appl. No. 11/037,548.
USPTO Office Action dated Nov. 14, 2007 in U.S. Appl. No. 10/912,578.
USPTO Office Action dated Nov. 28, 2007 in U.S. Appl. No. 11/234,395.
USPTO Office Action dated Dec. 6, 2007 in U.S. Appl. No. 11/037,548.
USPTO Office Action dated Dec. 10, 2007 in U.S. Appl. No. 10/912,578.
USPTO Office Action dated Jan. 24, 2008 in U.S. Appl. No. 10/259,300.
USPTO Office Action dated Apr. 9, 2008 in U.S. Appl. No. 11/037,548.
USPTO Office Action dated Sep. 12, 2008 in U.S. Appl. No. 10/829,917.
USPTO Office Action dated Oct. 6, 2008 in U.S. Appl. No. 10/259,300.
USPTO Office Action dated Oct. 29, 2008 in U.S. Appl. No. 11/347,147.
USPTO Office Action dated Nov. 7, 2008 in U.S. Appl. No. 10/944,270.
USPTO Office Action dated Nov. 17, 2008 in U.S. Appl. No. 10/829,917.
USPTO Office Action dated Nov. 17, 2008 in U.S. Appl. No. 12/117,582.
USPTO Office Action dated Nov. 17, 2008 in U.S. Appl. No. 12/118,931.
USPTO Office Action dated Nov. 25, 2008 in U.S. Appl. No. 12/117,961.
USPTO Office Action dated Dec. 5, 2008 in U.S. Appl. No. 12/120,902.
USPTO Office Action dated Jan. 28, 2009 in U.S. Appl. No. 10/944,270.
USPTO Office Action dated Feb. 4, 2009 in U.S. Appl. No. 11/347,147.
USPTO Office Action dated Mar. 3, 2009 in U.S. Appl. No. 12/117,582.
USPTO Office Action dated Mar. 4, 2009 in U.S. Appl. No. 12/118,931.
USPTO Office Action dated Mar. 17, 2009 in U.S. Appl. No. 11/690,127.
USPTO Office Action dated Mar. 18, 2009 in U.S. Appl. No. 10/829,917.
USPTO Office Action dated Mar. 23, 2009 in U.S. Appl. No. 11/804,309.
USPTO Office Action dated Mar. 23, 2009 in U.S. Appl. No. 11/926,326.
USPTO Office Action dated Apr. 21, 2009 in U.S. Appl. No. 10/944,270.
USPTO Office Action dated Jul. 30, 2009 in U.S. Appl. No. 12/118,931.
USPTO Office Action dated Aug. 6, 2009 in U.S. Appl. No. 11/347,147.
USPTO Office Action dated Aug. 6, 2009 in U.S. Appl. No. 12/117,582.
USPTO Office Action dated Aug. 6, 2009 in U.S. Appl. No. 12/117,961.
USPTO Office Action dated Aug. 28, 2009 in U.S. Appl. No. 11/150,847.
USPTO Office Action dated Oct. 21, 2009 in U.S. Appl. No. 12/120,902.
USPTO Office Action dated Nov 9, 2009 in U.S. Appl. No. 10/829,917.
Argon Medical. Maxxim Medical. Ad for Sniper EliteTM Hydrophilic Ni-Ti Alloy Guidewire (2001).
Aust, R., et al. 'The Functional Size of the Human Maxillary Ostium in Vivo' Acta. Otolaryn. (9178) vol. 78 pp. 432-435.

(56) References Cited

OTHER PUBLICATIONS

Baim, D.S., MD 'Grossman's Cardiac Catheterization, Angiography, and Intervention'.(2000) Lippincott Williams & Wilkins pp. 76, 84 & 214.

Becker, A.E. 'Restenosis After Angioplasty' The Lancet (1988) vol. 331, No. 8584 p. 532.

Bellis, M. History of the Catheter-Balloon Catheter-Thomas Fogarty. Www.inventors.about.com/library/inventors/blcatheter.htm?p=1.

Brown, C.L. et al., 'Safety and Feasibility of Balloon Catheter Dilation of Paranasal.Sinus Ostia: A Preliminary Investigation' Annals of Otology, Rhinology & Laryngology.(2006) vol. 115, No. 4 pp. 293-299.

Casserly, I.P. et al., Chapter 7. 'Guides and Wires in Percutaneous Coronary Intervention' Strategic Approaches in Coronary Intervention (2006) Lippincott Williams & Wilkins pp. 91-99.

ENT Checklist; Physical Examination Performance Checklist [date of publication unknown].

Feldman, R.L. et al., 'New Steerable, Ultra-Low-Profile, Fixed Wire Angioplasty Catheter: Initial Experience With the Cordis OrionTM Steerable PTCA Balloon Catheter' Cathet. Cardiovasc. Diagn. (1990) vol. 19, No. 2 pp. 142-145.

Ford, C.N. 'A Multipurpose Laryngeal Injector Device' Otolaryngol. Head Neck Surg. (1990) vol. 103, No. 1 pp. 135-137.

Gupta, D. et al., 'Dacrystitis Secondary to an Iatrogenic Foreign Body in the Lacrimal Apparatus' Ear, Nose & Throat Journal (2009) www.findarticles.com/p/articles/mi_m0BUM/is_7_88/ai_n32428620/.

Hopf, J.U.G. et al. 'Minature Endoscopes in Otorhinolaryngologic Applications' Min Invas Ther & Allied Technol. (1998) vol. 7, No. 3 pp. 209-218.

Hosemann, W. et al. A Dissection Course on Endoscopic Endonasal Sinus Surgery (2005) Endo-Press, Tuttlingen pp. 4-37.

Iro, H. et al., 'A New Device for Frontal Sinus Endoscopy: First Clinical Report' Otolaryngol. Head Neck Surg. (2001) vol. 125 No. 6 pp. 613-616.

Lang, E.V., et al., 'Access Systems for Puncture at an Acute Angle' J. Vasc. Interv.Radiol. (1995) vol. 6, No. 5 pp. 711-713.

Large, G.C. 'Crystalline Tetracycline Hydrochloride in the Treatment of Acute and Chronic Maxillary Sinusitis' Canad. M.A.J. (1958) vol. 79 pp. 15-16.

Mehan, V.K. et al., 'Coronary Angioplasty through 4 French Diagnostic Catheters' Cathet. Cardiovasc. Diagn. (1993) vol. 30, No. 1 pp. 22-26.

Metson, R., et al., 'Endoscopic Treatment of Sphenoid Sinusitis' Otolaryngol. Head Neck Surg. (1996) vol. 114, No. 6. pp. 736-744.

Mooney, M.R., et al., 'Monorail™ Piccolino Catheter: A New Rapid Exchange/Ultralow Profile Coronary Angioplasty System' Cathet. Cardiovasc. Diagn. (1990) vol. 20, No. 2 pp. 114-119.

Pownell, P.H. et al., 'Diagnostic Nasal Endoscopy' plastic & Reconstructive Surgery (1997) vol. 99, Iss5 pp. 1451-1458.

Ramsdale, D.R., Illustrated Coronary Intervention: A case-oriented approach, (2001) Martin Dunitz Ltd. pp. 1-5.

Ritter, F.N. et al., Atlas of Paranasal Sinus Surgery (1991) Igaku-Shoin Medical Pub. pp. 1-81.

Sama, A., et al., 'Current Opinions on the Surgical Management of Frontal Sinus Disease' ENT News. www.pinpointmedical.com/ent-news (2009) vol. 17, No. 6 pp. 60-63.

Sanborn, T.A. et al., 'Percutaneous Endocardial Transfer and Expression of Genes to the Myocardium Utilizing Fluropscopic Guidance' Catheter Cardiovasc. Interv. (2001) vol. 52, No. 2 pp. 260-266.

Saxon, R.R. et al., 'Technical Aspects of Accessing the Portal Vein During the TIPS Procedure' J. Vasc. Interv. Radiol. (1997) vol. 8, No. 5 pp. 733-744.

Schneider. Pfizer Ad for Softip [date of publication unknown].

Shah, N.J. et al., 'Endoscopic Pituitary Surgery—A Beginner's Guide' Indian Journal of Otolaryngology and Head and Neck Surgery (2004) vol. 56, No. 1 pp. 71-78.

SurgTrainer Product Information 'Incisive Human Nasal Model for ESS Training' Surg Trainer, Ltd. Ibaraki, Japan (2004) www1.accsnet.ne.jp/~juliy/st/en/partslist.html.

Tabor, M.H. et al., 'Symptomatic Bilateral Duct Cysts in a Newborn—Rhinoscopic Clinic' Ear, Nose & Throat Journal (2003) www.findarticles.com/p/articles/mi_m0BUM/is_2_82/ai_98248244 pp. 1-3.

Terumo. Medi-Tech. Boston Scientific. (1993) Ad of Glidewire.

Weiner, R.I., D.O., et al., 'Development and Application of Transseptal Left Heart Catheterization' Cathet. Cardiovasc. Diagn. (1988) vol. 15, No. 2, pp. 112-120.

Wiatrak, B.J., et al., 'Unilateral Choanal Atresia: Initial Presentation and Endoscopic Repair' International Journal of Pediatric Otorhinolaryngology (1998) vol. 46, pp. 27-35.

Wormald, P.J., et al., 'The 'Swing-Door' Technique for Uncinectomy in Endoscopic Sinus Surgery' The Journal of Laryngology and Otology (1998) vol. 112, pp. 547-551.

Xomed-Treace. Bristol-Myers Squibb. Ad for Laser Shield II. Setting the Standards for Tomorrow. [date of publication unknown].

Yamauchi, Y., et al., 'A Training System for Endoscopic Sinus Surgery with Skill Evaluation' Computer Assisted Radiology and Surgery (2001) with accompanying poster presentation.

Zimarino, M., M.D., et al., 'Initial Experience with the Europass™: A new Ultra-Low Profile monorail Balloon Catheter' Cathet. Cardiovasc. Diagn. (1994) vol. 33, No. 1, pp. 76-79.

Australian Office Action, Examiners First Report dated Dec. 9, 2011 for Application No. AU 2006292818.

Chinese Office Action, First Office Action dated Nov. 5, 2012 for CN 200980137396.1.

Chinese Search Report dated Oct. 29, 2012 for Application No. CN 200980137396.1.

Chinese Search Report dated Jan. 11, 2013 for Application No. CN 200980152995.0.

Chinese Office Action, First Office Action dated Jan. 29, 2013 for CN 200980152995.1.

European Communication dated Aug. 1, 2012 for Application No. EP 06784759.0.

European Communication dated Aug. 24, 2012 for Application No. EP 05798331.4.

European Communication dated Nov. 9, 2012 for Application No. EP 07750248.2.

European Communication dated Apr. 19, 2012 for Application No. EP 08746715.5.

European Communication dated Jan. 7, 2013 for Application No. EP 08746715.5.

European Communication dated Apr. 11, 2013 for Application No. EP 05778834.1.

European Search Report dated Jan. 11, 2013 for Application No. EP 12183002.

European Search Report dated Jan. 9, 2013 for Application No. EP 12183000.

European Search Report dated Dec. 5, 2012 for Application No. EP 12182998.

European Search Report dated Nov. 22, 2012 for Application No. EP 12182993.

European Search Report dated Oct. 10, 2012 for Application No. EP 12175607.

European Search Report dated Aug. 31, 2012 for Application No. EP 12173295.

European Search Report dated Jul. 24, 2012 for Application No. EP 12162712.

European Search Report dated Jul. 23, 2012 for Application No. EP 12162709.

European Search Report dated Sep. 27, 2011 for Application No. EP 10182961.

European Search Report dated Sep. 29, 2011 for Application No. EP 10182893.

Partial European Search Report dated Sep. 20, 2007 for Application No. EP 07252018.

Partial European Search Report dated Mar. 25, 2008 for Application No. EP 07252018.

Supplemental Partial European Search Report dated Jul. 1, 2009 for Application No. EP 06815285.

Supplemental European Search Report dated Jan. 29, 2010 for Application No. EP 07836108.

(56) References Cited

OTHER PUBLICATIONS

Supplemental European Search Report dated Mar. 16, 2010 for Application No. EP 06718986.
Supplemental European Search Report dated Sep. 23, 2010 for Application No. EP 08746715.
Supplemental European Search Report dated Jan. 28, 2011 for Application No. EP 07777004.
Supplemental European Search Report dated Mar. 31, 2011 for Application No. EP 05798331.
Supplemental European Search Report dated Aug. 30, 2011 for Application No. EP 06800540.
Supplemental European Search Report dated Sep. 29, 2011 for Application No. EP 07750248.
International Preliminary Report on Patentability dated Jun. 29, 2011 for Application No. PCT/US2009/069143.
International Search Report dated May 8, 2007 for Application No. PCT/US2006/16026.
International Search Report dated Sep. 25, 2007 for Application No. PCT/US06/37167.
International Search Report dated Oct. 19, 2007 for Application No. PCT/US07/03394.
International Search Report dated Jul. 3, 2008 for Application No. PCT/US2006/029695.
International Search Report dated Jul. 8, 2008 for Application No. PCT/US07/11474.
International Search Report dated Sep. 10, 2008 for Application No. PCT/US07/16212.
International Search Report dated Oct. 15, 2008 for Application No. PCT/US2008/061048.
International Search Report dated Nov. 30, 2009 for Application No. PCT/US2009/057203.
International Search Report dated Jul. 8, 2010 for Application No. PCT/US2010/027837.
International Search Report and Written Opinion dated Oct. 6, 2010 for Application No. PCT/US2010/040548.
International Search Report dated Mar. 25, 2011 for Application No. PCT/US2010/062161.
International Search Report dated Mar. 28, 2011 for Application No. PCT/US2010/061850.
International Search Report dated Mar. 31, 2011 for Application No. PCT/US2010/060898.
International Search Report dated Aug. 9, 2011 for Application No. PCT/US2011/038751.
International Search Report dated May 18, 2012 for Application No. PCT/US2011/052321.
Japanese Office Action, Examiner's Decision of Refusal dated Oct. 18, 2011 for Application No. JP 2007-509632.
Japanese Office Action, Notification of Reasons for Refusal dated Apr. 26, 2011 for Application No. JP 2007-532485.
Japanese Office Action, Notification of Reasons for Refusal dated Jan. 24, 2012 for Application No. JP 2007-532485.
Japanese Office Action, Notification of Reasons for Refusal dated Aug. 16, 2011 for Application No. JP 2008-516013.
Japanese Office Action, Notification of Reasons for Refusal dated Nov. 8, 2011 for Application No. JP 2008-524250.
Russian Office Action dated Sep. 28, 2012 for Application No. RU 2011130530.
Russian Office Action dated Mar. 19, 2013 for Application No. RU 2011130530.
USPTO Office Action dated Dec. 29, 2008 for U.S. Appl. No. 11/193,020.
USPTO Office Action dated May 13, 2009 for U.S. Appl. No. 11/193,020.
Gottman, et al., Balloon Dilatation of Recurrent Ostial Occlusion of the Front Sinus OASIS-Online Abstract Submission and Invitation System, 1996-2006, Coe Truman Technologies, Inc.
Sinusitis, Maxillary, Acute Surgical Treatment. http://www.emedicine.com/ent/topic340.htm. Aug. 29, 2006. pp. 1-11.
Strohm, et al 'Le Traitement des Stenoses Voies Aeriennes Superieures Par Dilation Ay Balloon' Sep. 25, 1999.
European Communication dated May 10, 2013 for Application No. EP 06751637.7.
European Search Report dated Aug. 13, 2013 for Application No EP 13172140.
European Search Report dated Sep. 9, 2013 for Application No. EP 13179223.
International Search Report dated Mar. 31, 2010 for Application No. PCT/US2009/069143.
Partial International Search Report dated Feb. 7, 2012 for Application No. PCT/US2011/052321.
Japanese Office Action, Notification of Reasons of Refusal dated Jun. 25, 2013 for Application No. JP 2012-131840.
U.S. Appl. No. 11/648,158, filed Dec. 29, 2006.
U.S. Appl. No. 11/804,308, filed May 16, 2007.
U.S. Appl. No. 11/804,309, filed May 16, 2007
U.S. Appl. No. 13/840,430, filed Mar. 15, 2013.
English Machine Translation of Japanese Patent Publication No. JP5-503650.
Japanese Office Action, Notification of Reasons for Refusal dated Sep. 18, 2013 for Application No. JP2011-527942.
U.S. Appl. No. 11/804,308, filed May 16, 2007
U.S. Appl. No. 11/804,309, filed May 16, 2007.

\* cited by examiner

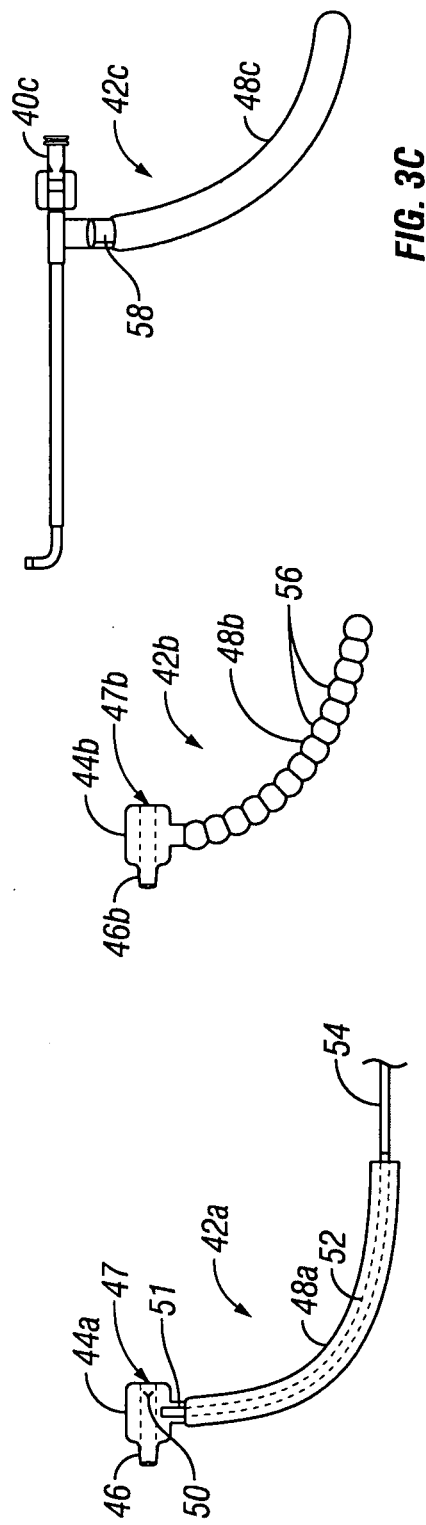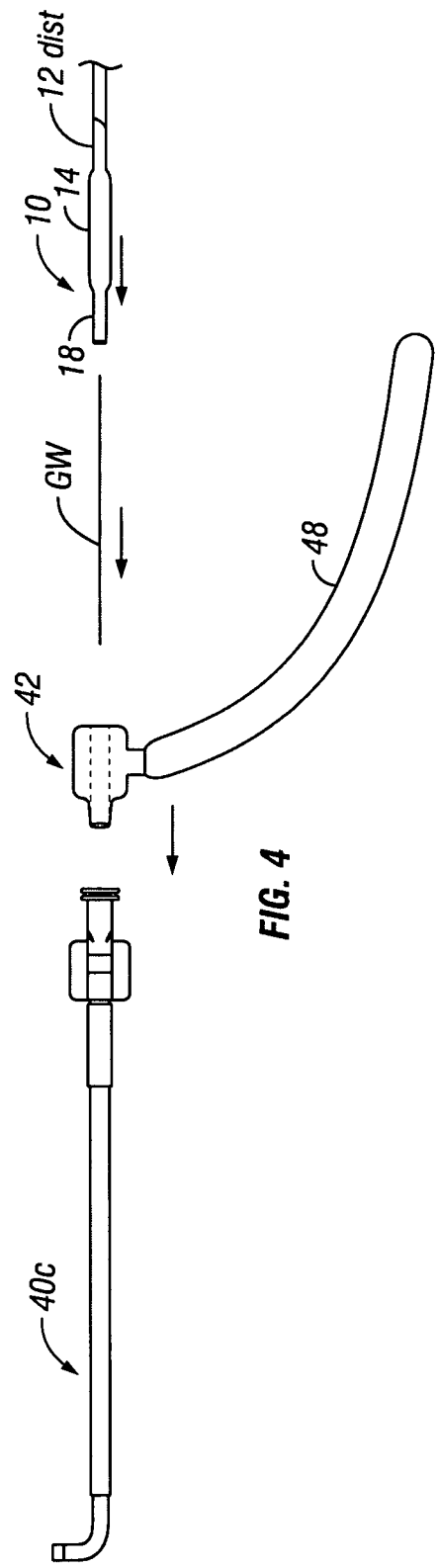
FIG. 3C
FIG. 3B
FIG. 3A
FIG. 4

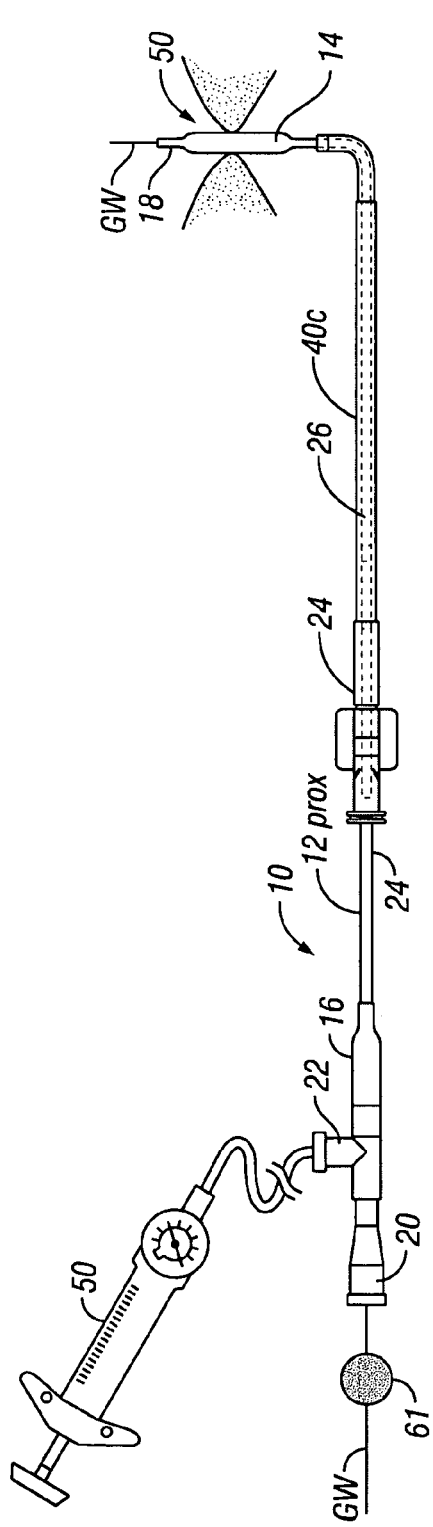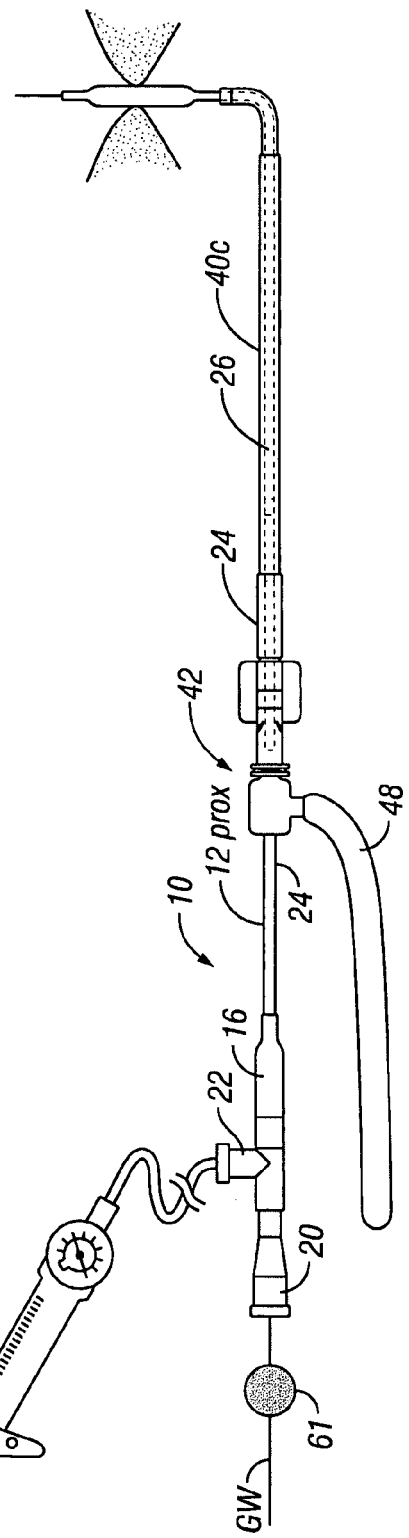

SYSTEMS FOR TREATING DISORDERS OF THE EAR, NOSE AND THROAT

RELATED APPLICATIONS

This application is a continuation in part of copending U.S. patent application Ser. No. 11/355,512 entitled "Devices, Systems and Methods Useable for Treating Frontal Sinusitis" filed Feb. 16, 2006, which is a is a continuation in part of Ser. No. 11/150,874 entitled "Devices, Systems and Methods Useable for Treating Sinusitus" filed on Jun. 10, 2005, which is a continuation in part of Ser. No. 10/944,270 entitled "Apparatus and Methods for Dilating and Modifying Ostia of Paranasal Sinuses and Other Intranasal or Paranasal Structures" filed on Sep. 17, 2004, which is a continuation in part of Ser. No. 10/829,917 entitled "Devices, Systems and Methods for Diagnosing and Treating Sinusitis and Other Disorders of the Ears, Nose and/or Throat" filed on Apr. 21, 2004, the entire disclosures of each such application being expressly incorporated herein by reference.

FIELD OF THE INVENTION

The present invention relates generally to medical devices and methods and particularly to balloon catheters other devices that may be inserted through the nose and used to dilate the ostia of paranasal sinuses for treatment of sinusitis.

BACKGROUND

The paranasal sinuses are hollow cavities in the skull connected by small openings, known as ostia, to the nasal canal. Normally, air passes into and out of the paranasal sinuses through the ostia. Also, mucus is continually formed by the mucosal lining of the sinus and drains through the ostia and into the nasal canal.

Sinusitis is a general term that refers to inflammation in one or more of the paranasal sinuses. Acute sinusitis can be associated with upper respiratory infections or allergic conditions which cause tissue swelling and temporarily impedes normal trans-ostial drainage and ventilation of the sinuses, thereby resulting in some collection of mucous and possibly infection within the sinus cavities. Chronic sinusitis is a long term condition characterized by persistent or long term narrowing or blockage of the sinus ostia, resulting in chronic infection and inflammation of the sinuses. Chronic sinusitis is often associated with long standing respiratory allergies, nasal polyps, hypertrophic nasal turbinates and/or deviated internasal septum. While acute sinusitis is typically caused by infection with a single pathogen (e.g., one type of bacteria, one type of virus, one type of fungus, etc.), chronic sinusitis is often associated with multiple pathogen infections (e.g., more than one type of bacteria or more than genus of microorganism).

Chronic sinusitis, if left untreated, can result in irreparable damage to the tissues and/or bony structures of the paranasal anatomy. The initial treatment of chronic sinusitis usually involves the use of drugs such as decongestants, steroid nasal sprays and antibiotics (if the infection is bacterial). In cases where drug treatment alone fails to provide permanent relief, surgical intervention may be indicated.

Functional endoscopic sinus surgery (FESS) is commonly performed use an endoscope and various rigid instruments inserted through the patient's nostril. The endoscope is used to visualize the positioning and use of the operative instruments to perform tasks intended to improve sinus drainage, such as removal of polyps, straightening of deviated septum and excision of mucous membrane and bone to enlarge the narrow the sinus ostia or to create new openings into the sinuses.

Recently technique known as the Balloon Sinuplasty™ procedure has been developed by Acclarent, Inc. of Menlo Park, Calif. for treatment of sinusitis. A number of copending U.S. patent applications, including parent applications Ser. No. 11/355,512, 11/150,874, 10/944,270 and 10/829,917, describe various embodiments of the Balloon Sinuplasty™ procedure as well as various devices useable in the performance of such procedure. In the Balloon Sinuplasty™ procedure, a guide catheter is inserted into the nose and positioned within or adjacent to the ostium of the affected paranasal sinus. A guidewire is then advanced through the guide catheter and into affected paranasal sinus. Thereafter, a dilation catheter having an expandable dilator (e.g., an inflatable balloon) is advanced over the guidewire to a position where the dilator is positioned within the ostium of the affected paranasal sinus. The dilator is then expanded causing dilation of the ostium and remodeling of bone adjacent to the ostium, without required incision of the mucosa or removal of any bone. The catheters and guidewire are then removed and the dilated ostium allows for improved drainage from and ventilation of the affected paranasal sinus.

Parent applications Ser. No. 11/355,512, 11/150,874, 10/944,270 and 10/829,917 also describe methods for transnasal dilation of other passageways in the ear, nose and/or throat, such as the Eustachian tube and nasolacrimal duct.

SUMMARY OF THE INVENTION

In accordance with the invention, there is provided a dilation catheter device and system that is useable for dilating the ostium of a paranasal sinus, or other passageway within the ear, nose or throat. This dilation catheter device and system is constructed in a manner that facilitates ease of use by the operator and, in at least some cases, allows the dilation procedure to be performed by a single operator, thereby minimizing the number of personnel required for the procedure. Additionally, the dilation catheter device and system of the present invention is useable in conjunction with an endoscope and/or a fluoroscope to provide for easy manipulation and positioning of the devices and real time visualization of the entire procedure or selected portions thereof. In some embodiments, an optional handle may be attached to the dilation catheter or to a guide catheter through which the dilation catheter is inserted and such handle may be graspable along with another device (e.g., an endoscope) by a single hand. In this manner, the operator may control the dilation catheter an another device (e.g., an endoscope) with one hand while being free to use his other hand for other purposes.

Further in accordance with the invention, there are provided systems for treating a disease or disorder of the ear, nose or throat of a human or animal subject. Such systems generally comprise a guide catheter and a working catheter. The working catheter is advanceable through the guide catheter. The guide catheter has a substantially rigid shaft and the working catheter has a proximal portion that is substantially rigid. The working catheter also has a distal portion that is more flexible than the substantially rigid proximal portion. The working catheter is sized relative to the guide catheter so that, at least when the distal portion of the working catheter is advanced out of a distal opening of the guide catheter and the working element is being used to perform a desired diagnostic or therapeutic task, only the substantially rigid proximal portion (or some portion thereof will extend out of the proximal opening of the guide catheter. In some embodiments, the working catheter may additionally be sized relative to the guide catheter so that the working catheter is initially advanceable to a first position where its distal end of the working catheter has not yet emerged out of the distal end of the guide catheter but only the substantially rigid proximal portion of the working catheter is protruding out of the proximal end of the guide catheter.

Still further in accordance with the invention, there are provided sinus ostium dilation catheter devices that generally comprise an elongate catheter shaft having proximal shaft section that is substantially rigid and a distal shaft section that is more flexible than the proximal shaft section. In some embodiments, the proximal shaft section may extend along at least about 50% of the overall length of the device. A guidewire lumen extends through at least a portion of the catheter shaft to facilitate advancement of the catheter over a guidewire. A dilator is located on the distal shaft section, such dilator having a non-expanded configuration and an expanded configuration.

Still further in accordance with the present invention there are provided methods for dilating the ostia of paranasal sinsus and other passageways within the ear, nose or throat of a human or animal subject. In general, such methods comprise the steps of a) inserting a guide catheter having a proximal end and a distal end through one of the subject's nostrils and positioning the guide catheter within or near the passageway to be dilated, b) inserting, through the guide catheter, a dilation catheter comprising i) an elongate catheter shaft having a proximal end, a distal end, a proximal shaft section that is substantially rigid and a distal shaft section that is more flexible than the proximal shaft section, ii) a guidewire lumen extending through at least a portion of the catheter shaft to facilitate advancement of the catheter over a that is substantially rigid and a distal shaft section that is more flexible than the proximal shaft section, ii) a guidewire lumen extending through at least a portion of the catheter shaft to facilitate advancement of the catheter over a guidewire and iii) a dilator located on the distal shaft section, said dilator being in a non-expanded configuration, c) positioning the dilator within the passageway and d) causing the dilator to expand to an expanded configuration, thereby dilating the passageway.

Still further embodiments, aspects, features and details of the present invention will be understood upon reading of the detailed description and examples set forth herebelow.

BRIEF DESCRIPTION OF THE DRAWINGS

FIG. 1A is a cross sectional view through line 1A-1A of FIG. 1 with an enlarged break-out view of a portion thereof.

FIG. 1B is an enlarged side view of the dilator and distal end of the dilation catheter of FIG. 1.

FIG. 3A is a side view of another embodiment of a handle apparatus of the present invention.

FIG. 3B is a side view of yet another embodiment of a handle apparatus of the present invention.

FIG. 3C is a side view of yet another embodiment of a handle apparatus of the present invention.

FIG. 4 is an exploded, partial view of one embodiment of a dilation catheter system of the present invention including an optional handle apparatus.

FIG. 5 is a schematic diagram of one embodiment of a dilation catheter system of the present invention (without the optional handle apparatus) being used to dilate the ostium of a paranasal sinus.

FIG. 6 is a schematic diagram of one embodiment of a dilation catheter system of the present invention (with the optional handle apparatus) being used to dilate the ostium of a paranasal sinus.

DETAILED DESCRIPTION

The following detailed description and the accompanying drawings are provided for the purpose of describing some, but not necessarily all, examples or embodiments of the invention. The contents of this detailed description and the accompanying drawings are exemplary in nature and do not limit the scope of the invention in any way.

A Dilation Catheter of the Present Invention

Figure 1:
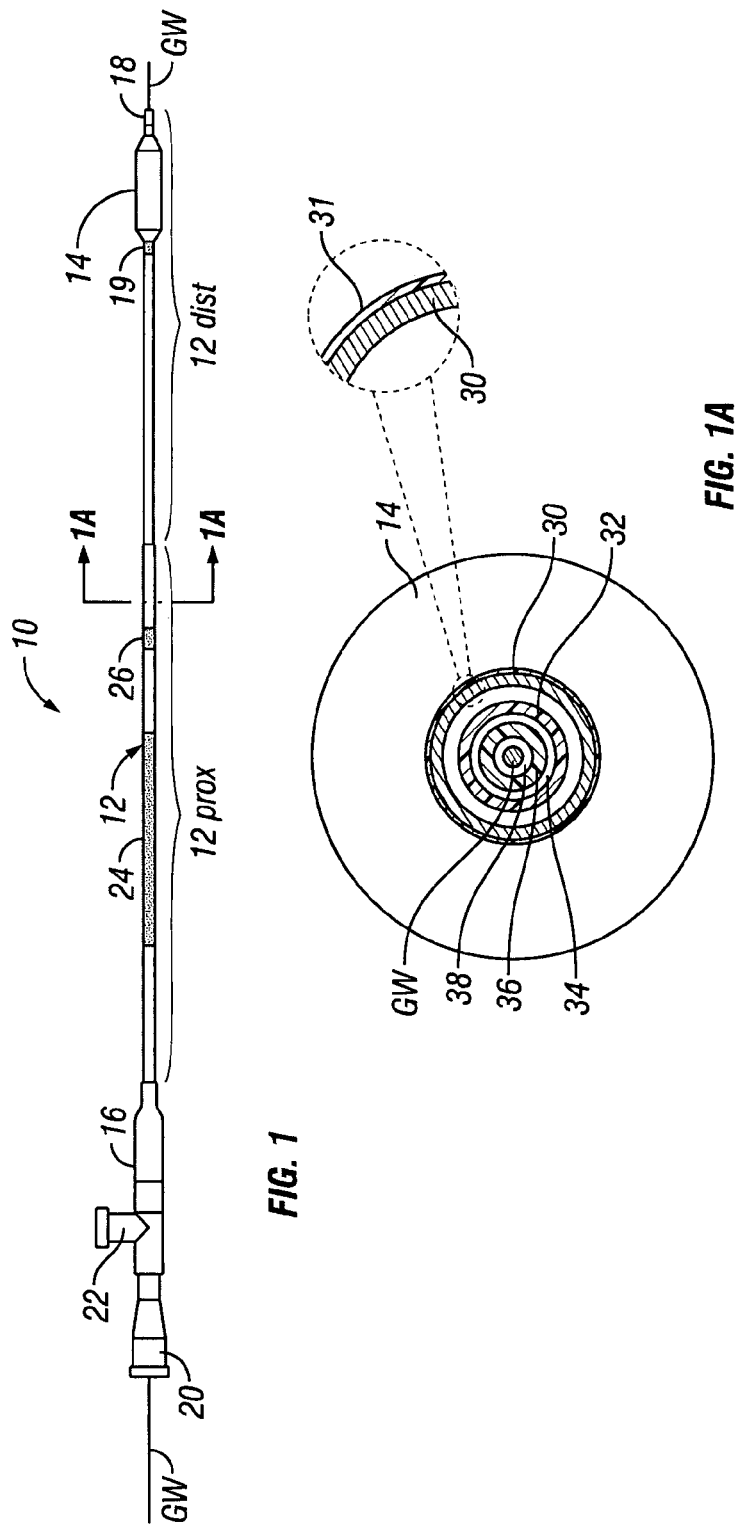
FIG. 1 is a side view of one embodiment of a dilation catheter of the present invention with its dilator in an expanded configuration.

FIGS. 1-1B show one example of a dilation catheter device 10 of the present invention with a guidewire GW operatively inserted therethrough. In this example, the dilation catheter device 10 comprises an elongate catheter shaft 12 having a proximal shaft section 12$prox$ that is substantially rigid and a distal shaft section 12$_{dist}$ that is more flexible than the proximal shaft section 12$_{prox}$. An expandable dilator, such as a balloon 14 or other suitable mechanical or non-inflational dilator, is mounted on the distal shaft section 12$_{dist}$ and a distal tip member 18 protrudes beyond the distal end of the balloon 14, as shown. Also, a proximal T hub 16 is attached to the proximal end of the proximal shaft section 12$_{prox}$. This proximal T hub 16 has a proximal Luer connector 20 and a side arm 22 having a female Luer connector that extends substantially perpendicular to the longitudinal axis of the hub 16, as shown. When compared to a typical Y hub, the side arm 22 of this T hub is further away from the proximal Luer connector 20 and is oriented at a right angle to the proximal Luer connector 20. Thus, tubing connected to this perpendicular side arm 22 is less likely to obscure or block the proximal Luer connector 20 than in a typical Y hub and the operator is less likely to confuse the proximal Luer connector 20 with the Luer connector on the side arm 22.

Although, in the particular example shown in the drawings, the expandable dilator comprises a balloon 14, it is to be appreciated that various other types of expandable dilators such as expandable cages, struts and other expandable mechanical assemblies may be used as an alternative to a balloon 14. Some non-limiting examples of expandable dilators other than balloons have previously been described in parent U.S. patent applications Ser. No. 11/355,512, 11/150, 874, 10/944,270 and 10/829,917, which are expressly incorporated herein by reference.

For use in teenage or adult humans, the overall length of the catheter shaft 12 may be in the range of about 15 cm to about 25 cm, the proximal shaft section $12_{prox}$ may have a length in the range of about 10 cm to about 15 cm and the distal shaft section $12_{dist}$ may have a length in the range of about 5 cm to about 10 cm. In the particular example shown in the drawings and described herein, the catheter shaft 12 has an overall length of 21.2 cm, the proximal shaft section $12_{prox}$ being 12.5 cm in length and the distal shaft section $12_{dist}$ being 8.7 cm in length. These optimal lengths of the proximal shaft section $12_{prox}$ and distal shaft section $12_{dist}$ have been arrived at based on a number of considerations, which will be discussed more fully herebelow in relation to the concurrent use of this dilation catheter 10 with a trans-nasal guide catheter.

As may be appreciated from the cross sectional view of FIG. 1A, the proximal shaft section $12_{prox}$ comprises a rigid outer tube 30 a flexible middle tube 32 disposed substantially coaxially within the lumen of the rigid outer tube 30 and an inner tube 36 disposed substantially coaxially within the lumen of the middle tube 32. In this particular example, the outer tube 30 is formed of stainless steel hypotube having an outer diameter of 0.076 inches and an inner diameter of 0.068 inches. As an alternative to stainless steel hypotube, this outer tube 30 may be formed of rigid non-metallic material such as polyetheretherketone (PEEK) or other rigid plastics suitable for such application. Alternatively, other rigid reinforcing members may be used in, or in lieu of, the outer tube, such as wires (round, flat, square or of other cross section), partial tubes (e.g., arcs), etc. Also, in this particular example, the middle tube 32 is formed of Pebax having an inner diameter of 0.055 inches, an outer diameter of 0.065±0.003 inches. The inner tube 36 is formed of polyether block copolymer tubing (e.g., Pebax® Resin, Arkema, Inc., Philadelphia, Pa.) having an inner diameter of 0.038 inches, an outer diameter of 0.048 inches.

The outer tube 30 terminates at the end of the proximal shaft section $12_{prox}$. The middle tube 32 and inner tube 36 extend beyond the distal end of the outer tube 30, forming the distal shaft section $12_{dist.}$ As seen in the enlarged break-out segment of FIG. 1A, a polyether block copolymer film laminate 31 (e.g., Pebax® Resin, Arkema, Inc., Philadelphia, Pa.) is heat shrunk onto the outer surface of the catheter shaft 12 from the proximal hub 16 to the balloon 14. This laminate 31 provides a smooth outer surface and smoothes the step-down in diameter from the distal end of the proximal shaft section $12_{prox}$ to the proximal end of the distal shaft section $12_{dist}$ (i.e., it provides a smooth surface over the distal end of the outer tube 30 and the adjacent outer surface of the middle tube 32). The smooth step down may also be formed by an adhesive fillet. In other embodiments, the smooth step down may be formed by tapering or chamfering the structure of the distal end of the proximal shaft, eliminating the need for a laminate or adhesive.

The proximal end of the middle tube 32 extends into and is secured to the hub 16, distal to side arm Luer connector 22. The proximal end of the inner tube 36 extends into and is secured within hub 16, proximal to the side arm Luer connector 22 and in direct alignment and fluid communication with proximal Luer connector 20. The distal end of the middle tube 32 terminates within the balloon 14 and the proximal end of the dilator is secured to the outer surface of the middle tube. The distal end of the inner tube 36 also extends through the balloon 14 and protrudes distally beyond the balloon 14, forming the relatively flexible distal tip member 18 as shown in FIG. 1. The distal end of the balloon 14 is secured to the outer surface of the inner tube 36. In this manner, the inner tube lumen 38 extends through the entire catheter shaft 12 from the proximal Luer connector 20 through the distal tip 18 and may be used a guidewire lumen or as a working lumen for infusion of irrigation solution, medicaments, contrast media or other substances and/or for aspiration of blood, fluids or debris. Guidewires that may be advantageously used in conjunction with this dilation catheter 10 may have a length of 60 cm to 80 cm and may be either 0.014 inch or 0.035 inch, such as those commercially available as the Relieva® Sinus Guidewires (Acclarent, Inc., Menlo Park, Calif.) or sizes in between such as 0.018 inch, 0.020 inch, or 0.033 inch. Although the drawings show an over-the-wire catheter having a guidewire lumen that extends through the entire length of the catheter, it is to be appreciated that guidewire lumens extending less than the entire length of the catheter (e.g., rapid exchange guidewire lumens) may be used as an alternative to the over-the-wire lumen shown. Additionally, in some embodiments, rather than advancing the catheter over a guidewire, the catheter may be equitted with a fixed guidewire tip such as any of those described in U.S. patent application Ser. No. 11/438,090 entitled Catheters with Non-Removable Guide Members Useable for Treatment of Sinusitis, the entire disclosure of which is expressly incorporated herein by reference.

The inner tube lumen 38 may be lined or coated with a lubricious material to facilitate passages of the guidewire GW through that lumen 38. The diameter of the inner tube 36 may be changed to accommodate guidewires of different diameter. In the particular embodiment described, the inner tube lumen 38 is sized to receive a 0.035 inch diameter guidewire GW. The inner tube lumen 38 may be internally lined or coated with a 2% solution of linear polydimethylsiloxane (PDMS) (e.g., Dow Corning® 360 Medical Fluid, Dow Corning Corporation, Midland, Mich.) diluted in isopropyl alcohol or another silicone material (such as a 2% solution of Dow-Corning MDX4-4159 in isopropyl alcohol). The coating is cured at room temperature.

The luminal space 34 between the outer surface of the inner tube 36 and the inner surface of the middle tube 32 is in fluidic communication with the side arm Luer connector 22 and extends to the interior of the balloon 14. Thus, this luminal space 34 serves as the passageway through which inflation fluid is passes into and out of the balloon 14. The size of this luminal space 34 and the relatively short length of the catheter shaft 12 are optimized to minimize drag on inflation fluid passing through this luminal space 34 and allows for rapid deflation of the balloon 14. The clearance of 0.006 to 0.007 inches between the inner and outer member is desired for catheter length of 20-35 cm. The desired deflation time is 5-10 seconds and the deflation time is measured with application of negative pressure on the inflation/deflation lumen using a 20 cc inflation device that is filled with 10 cc contrast/saline mixture.

Balloon Construction and Coating

FIG. 1B shows details of the balloon 14. In this example, the balloon 14 is a non-compliant balloon formed of polyethylene teraphthalate (PET) film having a thickness of 0.8 mils. The balloon 14 has a cylindrical midregion 44 and tapered proximal and distal end regions $46_{prox}$ and $46_{dist}$. The balloon 14 has an overall length of 2.6 cm. The cylindrical midregion 44 of the balloon 14 has a length of 16 mm (i.e., the "working length") and each tapered end region $46_{prox}$, $46_{dist}$ has a length of 5 mm. The balloon 44 has a burst pressure of at least 14 to 16_ atmospheres. The outer diameter of the balloon 14, when inflated to a pressure of 14 atmospheres, may be in the range of 5.0 mm to 5.5 mm. In this particular example, the balloon 14 is sized for dilation of the ostia of paranasal sinuses and such balloon 14 is offered in sizes having outer diameters of 5 mm or 7 mm when inflated to a pressure of 14 atmospheres. Dilation catheters 10 having the 5 mm diameter balloon 14 may be more suitable for use in subjects of small body size while dilation catheters 10 having the 7 mm diameter balloon 14 may be more suitable for use in subjects having a large body size. Smaller or larger balloons may be used for dilating structures other than the ostia of paranasal sinuses (e.g., Eustachian tube or naso-lacrimal duct dilations). Larger balloons and higher pressures may be used for dilating revision patients (i.e., patients who have had prior ostial dilations or who's ostia have been previously modified by surgery).

The tapered end regions $46_{prox}$, $46_{dist}$ are tapered at angle A relative to the longitudinal axis LA of the catheter shaft 12 on which the balloon 14 is mounted. This angle of taper A may be in the range of about 10 degrees to about 30 degrees. In the particular example shown in the drawings, such angle of taper A is 20 degrees. This 20 degree angle of taper provides improved transition from balloon working length to the necks, lower profile, improved crossing, improved track, easier withdrawal in the sinus guide after balloon inflation. It also provides optimal performance with minimum increase of overall balloon length.

In some embodiments, it may be desirable for the relatively stiff proximal shaft portion $12_{prox}$ to extend all the way to or near the proximal end of the balloon 14 or other dilator. Such catheter having a rigid shaft from its proximal end to or near the dilator may be advanced directly into the sphenoid sinus ostium with or without the use of a guide catheter. In some embodiments, the proximal end of the balloon 14 could be bonded to the relatively rigid proximal shaft portion 12prox. Such a construction would allow the flexible distal tip 18 to track turns in the anatomy and may be useable to dilate certain passageways (e.g., the sphenoid sinus ostium) without disrupting the normal anatomy. Additionally, embodiments with relatively short distal shaft sections (e.g., 1-2 cm beyond the distal end of the rigid proximal shaft portion are particularly suitable for dilating the ostia of frontal sinuses. Also, in some embodiments, the proximal shaft section 12prox may be malleable so that it may be shaped (e.g., bent or formed to a desire curve or multi-curvate shape) to facilitate access to any desired passageways or locations.

Dilation Catheter/Guide Catheter System

Figure 2:
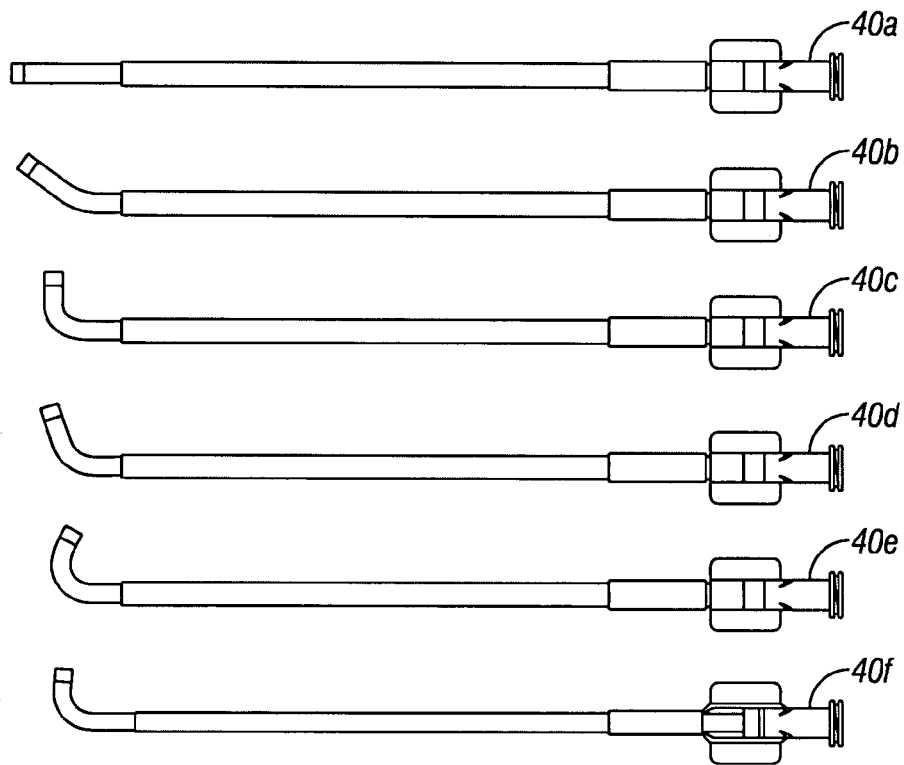
FIG. 2 shows a collection of transnasal guide catheters useable as components of the system of the present invention.

FIG. 2 shows a series of sinus guide catheters 40a-40f that may be used in conjunction with the dilation catheter 10. These guide catheters 40a-40f are substantially rigid and each has a preset distal curve of 0 degrees (40a), 30 degrees (40b), 90 degrees (40d), 70 degrees (40c) or 110 degrees (40e and 40f). Different curvatures are useable to access the ostia of different sinuses. For example, a 70 degree guide is typically used to access the ostium of a frontal sinus, a 90 or 110 degree guide is typically used to access the ostium of a maxillary sinus, etc. Each of these guide catheters 40a-40f has a length of 12.7 cm. These sinus guide catheters are described in parent U.S. patent application Ser. Nos. and are now commercially available as Relieva® sinus guide catheters from Acclarent, Inc., Menlo Park, Calif.

FIG. 5 shows a system comprising a guide catheter 40c having a 90 degree curve formed therein in combination with a dilation catheter 10 shown in FIG. 1. In optimizing the relative lengths of the proximal shaft section $12_{prox}$ and distal shaft section $12_{dist}$, applicants have determined that, even the maximum distance that the distal end of the dilation catheter of this example is required travel beyond the distal end of the guide catheter 40a-40c is approximately 2.5 cm. However, it will be appreciated that this is just one example. For other application, travel beyond 2.5 cm may be desirable or necessary. Also, it is desirable for the entirety of the more flexible distal shaft section $12_{dist}$ to be advanceable into the guide catheter 40a-40f proximal to any curve formed in the guide catheter. With these objectives in mind, the example of the dilation catheter 10 shown in the drawings has a shaft that is about 20 cm in length, with the proximal shaft section $12_{prox}$ being 11.3 cm in length and the distal shaft section $12_{dist}$ being 8.7 cm in length. Thus, prior to or during the procedure, the entire distal shaft section $12_{dist}$ of the dilation catheter 10 may be initially advanced into the rigid guide catheter 40c without the distal portion of the dilation catheter 10 passing through the curve of the guide catheter 40c and with only a portion of the rigid proximal shaft section $12_{prox}$ of the dilation catheter 10 protruding out of the proximal end of the guide catheter 40c. To facilitate such positioning of the dilation catheter 10 within the guide catheter 40d, a first shaft marker 26 is provided on the proximal shaft section $12_{prox}$ of the dilation catheter shaft 12. The distal edge of this first shaft marker 26 is 2.7 cm proximal to the distal end of the proximal shaft section $12_{prox}$ and 11.4 cm from the distal end of the distal tip member 18. If the operator advances the dilation catheter 10 into the guide catheter 40c until the distal edge of the first shaft marker 26 is flush with the proximal end of the guide catheter 40c, the entire distal shaft portion 12dist as well as the distal-most 3 cm of the proximal shaft portion $12_{prox}$ will be housed within the guide catheter 40c such that the distal end of the dilation catheter 10 is located proximal to the curve formed near the distal end of the guide catheter 40c. Such positioning of the dilation catheter 10 within the guide catheter 40c provides a guide catheter/dilation catheter assembly that is substantially rigid from the proximal hub 16 of the dilation catheter 10 to the distal end of the guide catheter 40c. As a result, the operator may hold or support the entire assembly by grasping or supporting just one location on either the dilation catheter 10 or guide catheter 40d. For example, the user may hold or support the entire assembly by using his fingers to grasp or support either the proximal hub of the guide catheter 40c, the proximal hub 16 of the dilation catheter 10 or somewhere on the proximal shaft section $12_{prox}$ of the dilation catheter or on the shaft of the guide catheter 40c. Such rigidity also substantially eliminates the potential for the exteriorized portion of the dilation catheter 10 to droop down onto the subject's chest or onto the adjacent operating table.

As explained above, in this example, the rigid proximal shaft segment $12_{prox}$ of the dilation catheter 10 is 11.3 cm in length and the guide catheter 40d is 12.7 cm in length. Thus, when inserted into the subject's body, the overall length of the portion of the system that remains exteriorized (e.g., the proximal part of the guide catheter 10 extending out of the subject's nose and and the proximal part of the dilation catheter 10 extending out of the proximal end of the guide catheter 40c) is not only rigid, but sufficiently short (e.g., typically less than 9 cm) to be easily manageable and capable of being held or supported by a single hand of the operator, thereby allowing the operator's other hand to be used for other purposes, such as for advancing/retracting the guidewire GW or advancing/retracting the dilation catheter 10 in the manner described herebelow in connection with FIGS. 9-11.

The second shaft marker 24 correlates to the position of the balloon. If the dilation catheter 10 is advanced to a position where the distal edge of the second shaft marker 24 is flush with the proximal end of the guide catheter 10, the distal tip of the balloon catheter will be flush with the distal tip of the guide catheter 40d. When the proximal edge of the second shaft marker 24 is flush with the proximal end of the guide catheter 10, the entire balloon 14 will have advanced out of the distal end of the guide catheter 40d and the operator will know that it is safe to inflate the balloon. Typically, as seen in FIG. 5, the balloon 14 is advanced some distance out of the distal end of the guide catheter 40d until the balloon 14 is positioned within the sinus ostium SO or other passageway to be dilated. As seen in the enlarged view of the balloon 14 shown in FIG. 1B, proximal and distal radiographic markers 40, 42 are provided on the catheter at either end of the cylindrical segment 44 of the balloon. A C arm fluoroscope may be positioned and used to image those proximal and distal markers 40, 42 as well as the sinus ostium SO and the position of the dilation catheter 10 may be adjusted as needed until the sinus ostium SO is midway between the proximal and distal radiographic markers 40, 42. Thereafter, an inflator 50 attached to the side arm Luer connector 22 may be used to inflate the balloon 14, thereby dilating the sinus ostium SO as shown in FIG. 5. In keeping with the operator's ability to use a single hand to hold or support the exteriorized portion of the system, the inflator 50 may be attached to the side arm Luer connector 22 in advance and may be controlled by a foot pedal which is actuated by the operator's foot.

In some applications of the system shown in FIG. 5, an endoscope may be placed in the nose and used to view all or part of the procedure. Because the exteriorized portion of the system is substantially rigid and is typically less than 15 cm in length, the operator may use a single hand to hold the endoscope as well as the dilation catheter/guide catheter system. Alternatively, a scope holder may be used to hold the endoscope in a fixed position while the operator positions and uses the system seen in FIG. 5. Alternatively, an optional handle may be used as shown in FIGS. 3-4, 6 and 8A-8B and described below.

Optionally, a member 61 may be attached to the guidewire. Such member may serve to prevent the dilation catheter 10 and/or guide catheter 40a-40f from inadvertently sliding off of the proximal end of the guidewire. Also, such member 61 may limit the length of guidewire GW that may be advanced through the dilation catheter 10. This will prevent the operator from advancing too much of the guidewire GW into the subject's sinus, as may injure or damage the mucosa lining the sinus cavity. In some embodiments, this member 61 may be a standard guidewire torquer of the type commercially available an well known in the fields of interventional cardiology and/or radiology. One example of a commercially available guidewire torquer that is useable in this application is a two part torquer available as Part No. 97333 from Qosina, Corp., Edgewood, N.Y.

Figure 7A:
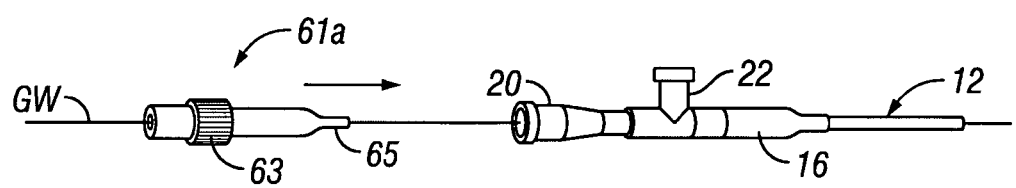
FIG. 7A shows a partial view of the system of FIG. 5 including a guidewire stop/connector apparatus of the present invention mounted on the guidewire prior to advancement of the guidewire.
Figure 7B:
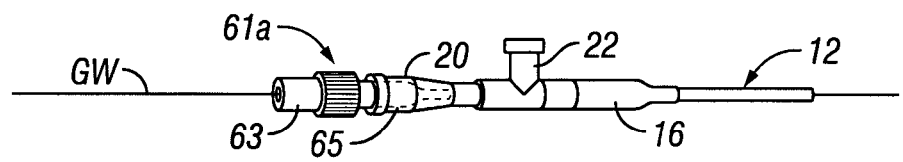
FIG. 7B shows a partial view of the system of FIG. 5 including a guidewire stop/connector apparatus of the present invention mounted on the guidewire and engaged with the hub of the dilation catheter following advancement of the guidewire.

Alternatively, the member 61 may comprise a guidewire stop/connector apparatus 61a as shown in FIGS. 7A-7B. This stop/connector apparatus 61a comprises a rigid plastic body 63 having a lumen extending therethrough and a tapered elastomeric tube member 65 on its distal end. The stop/connector apparatus 61a is advanced over the guidewire GW to the desired location. The inner diameter of the tapered elastomeric tube member 65 fits snuggly on the guidewire thereby holding the stop/connector apparatus 61a as seen in FIG. 7A. The guidewire GW is subsequently advanced through the dilation catheter 10 until the tapered elastomeric tube member 65 is received within and frictionally engages the proximal female Luer connector 20 on the hub of the dilation catheter, as shown in FIG. 7B. This limits advancement of the guidewire GW and also frictionally locks the guidewire GW to the dilation catheter 10 so that the operator may move both the guidewire GW and the dilation catheter 10 as a unit. If the operator decides to advance more of the guidewire into the sinus, the operator may grasp and move the stop/connector apparatus 61a by applying sufficient force to overcome the frictional engagement between the stop/connector apparatus 61a and the guidewire GW and/or between the stop/connector apparatus 61a and the guide catheter hub. The force required to overcome such frictional engagements will preferably be greater than the forces that would normally result form routine movement and use of the system, thereby allowing the stop/connector apparatus 61a to perform its locking function while still allowing the location of the stop/connector apparatus 61a to be volitionally adjusted by the operator when necessary.

Alternatively or additionally, if desired, another stop/connector apparatus 61a of larger size (or another suitable locking apparatus such as a Touhy-Borst valve) may be mounted on the rigid proximal shaft section 21prox of the dilation catheter 10 and received within the proximal end of the guide catheter 40a-f to limit the advancement of the dilation catheter 10 through the guide catheter 40a-f and to frictionally lock the dilation catheter 10 to the guide catheter 40a-f in the same manner.

Dilation Catheter/Guide Catheter System With Optional Handle

Figure 3:
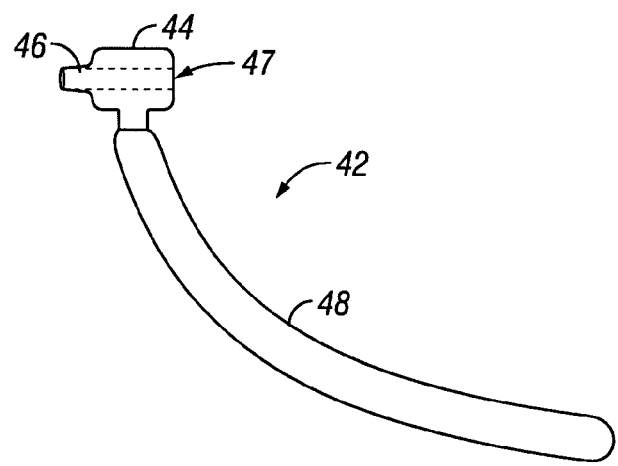
FIG. 3 is a side view of one embodiment of a handle apparatus of the present invention.

FIG. 3 shows an optional handle 42 that may be attached to the guide catheter 40a-40d to facilitate single-handed holding of the guide catheter/dilation catheter system as well as an endoscope (or other device). The handle shown in FIG. 3 comprises a rigid head 44 having a male Luer 10 fitting on one end, a lumen 47 extending therethrough and a handle member 48 extending therefrom. As seen in the exploded view of FIG. 4, the male Luer fitting 46 may be inserted into the proximal end of the guide catheter 40c and the guidewire GW and guide catheter 10 may then be inserted through the lumen 47 of the handle head 44 and through the guide catheter. The handle head 44 may be clear or transparent so that the operator may view the shaft markers 24, 26 on the dilation catheter shaft 12 as the dilation catheter 10 is advanced through the handle head 44. Alternatively, the locations of the shaft markers 24, 26 may be adjusted on the catheter shaft 12 to take into account the additional guide length added by the handle head 44. The handle member 48 is preferably about the size of a standard ink pen and may be conveniently grasped by a human hand. The handle member 48 may have a roughened or elastomeric surface to facilitate gripping by a gloved hand and to deter slippage of the handle from the operator's grip. The handle member 48 may be shapeable (e.g., malleable or bendable) to allow the operator to adjust the shape and/or angle of the handle relative to the shaft of the guide catheter 40c. In some embodiments, the handle member 48 may be pre-shaped to accommodate a typical user and allow fine tuning by individual user. Also, in some embodiments, the handle member 48 may have foam or other material on its surface to facilitate grip. The handle member 48 may have various different cross sectional profiles (e.g., round, oval, 3 sided, 4 sided, 5 sided, 6 sided, etc.) The handle 48 serves to facilitate grip and control to manipulate the dilation catheter along with a separate device (e.g., an endoscope or other tool) without having to use second hand. In this manner, the user may adjust rotation of a guide catheter while observing under endoscope (all with one hand) and use other hand to advance and place the guidewire or other device. Also, in some embodiments, the handle member 48 may include finger loop(s) for easier to translate handle/device attached up/down relative to other device held (e.g. scope) without need for other hand to adjust. Also, in some embodiments, a pinch valve or hole can be strategically placed in handle 48 to actuate/allow control of suction or fluid delivery via handle device (e.g., the user may pinch the handle with fingers to restrict flow through handle) or the handle 48 may have a suction hole where the user must cover the suction hole to actuate suction through the optional handle 42.

Alternative embodiments of the handle are shown in FIGS. 3A, 3B and 3C. FIG. 3A shows a handle 42a which is similar to that seen in FIG. 3, but wherein a fluid channel 52 extends from the lumen 47 downwardly through the head 44a and through the handle member 48a. A one way valve 50 is disposed within the lumen 47, proximal to the location where the fluid channel 52 meets the lumen 47. An irrigation and/or suction tube 54 may be attached to the handle member 48a to infuse fluid through or suction fluid and debris through the fluid channel 52. The one way valve will ensure that fluid infused or aspirated through the fluid channel 52 of the handle 42a will not escape out of the proximal opening of the lumen 47. However, this one way valve 50 does allow the guidewire GW and dilation catheter 10 to be inserted through the lumen 47, when desired. The one way valve may provide the additional benefit of maintaining the position of the guidewire or dilatation catheter when it is inserted in the guide handle. It will be appreciated that other types of valves other than a one-way valve may be used as an alternative (e.g., Touhy rotating type valve, slide to compress valve, etc.) Or, some embodiments may have just a valve and a thumb/finger hole to control the suction force as described above.]

FIG. 3B shows another embodiment of an optional handle 42b comprising a clear or transparent rigid head 44b having a male Luer fitting 46b on one end and a lumen 47 extending therethrough. In this embodiment, the handle member 48b is formed of a series or pivotally interconnected units 56 which allows the handle member 48b to be conveniently formed into various shapes as desired by the operator.

FIG. 3C shows yet another handle 42c comprising a malleable or rigid handle 48c that is substantially the same as that shown in FIG. 3, but wherein a clip 58 is provided at the top end of the handle member 48c to clip the handle member 48c onto the shaft of the guide catheter 40c rather than inserting into the proximal end of the guide catheter.

Figure 8A:
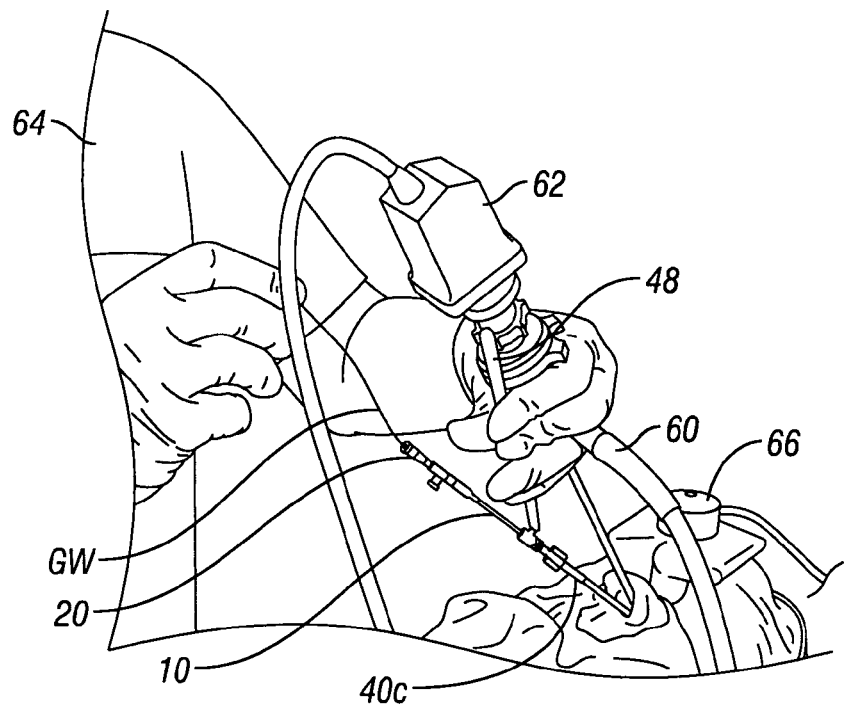
FIG. 8A shows the dilation catheter system of FIG. 5 and an endoscope being held by one hand of the operator while the operator's other hand is being used to advance the guidewire of the system into a paranasal sinus.
Figure 8B:
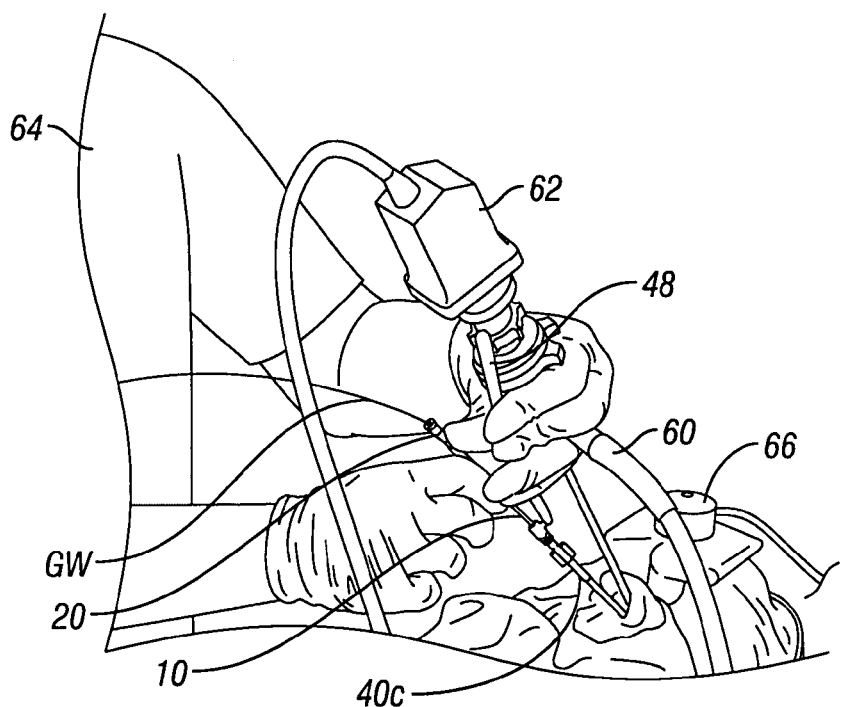
FIG. 8B shows the dilation catheter system of FIG. 6 and an endoscope being held by one hand of the operator while the operator's other hand is being used to advance the dilation catheter so that its dilator becomes positioned within the ostium of the paranasal sinus.

FIG. 6 shows the system of FIG. 5 with the inclusion of the optional handle 42 on the proximal end of the guide catheter 40c. FIGS. 8A and 8B show examples of how a handle 42 may be used to facilitate concurrent holding of an endoscope as well as the guide catheter (or guide catheter/dilation catheter assembly) by a single hand (i.e., the "scope hand") of the operator. With reference to FIGS. 5 and 8A-8B, the handle head 44 may initially be loosely inserted into the proximal hub of the guide catheter 40c. The camera 62 and light cable 66 are attached to the endoscope 60. While grasping the endoscope 60 in the manner shown in FIG. 8A, the operator may rotate the handle 42 relative to the guide catheter 40c to introduce the handle member 48 to the operator's scope hand. Alternatively, the handle member 48 could be grasped by the operator's scope hand along with the endoscope 60 upon initial introduction. When positioning of the endoscope 60 and guide catheter 40c have been achieved, the operator's other hand is used to push the male Luer fitting 46 of the handle 42 firmly into the female Luer fitting on the proximal end of the guide catheter 40c, thereby locking the handle 42 to the guide catheter 40c. Thereafter, the operator's other hand is used to manipulate the guidewire GW and dilation catheter 10. In this manner, the operator may maintain continuous endoscopic visualization via the endoscope 60 while using the guidewire GW and dilation catheter to dilate the ostium of a paranasal sinus or other passageway within the ear, nose or throat. As explained in more detail below, positioning of the guidewire GW and/or balloon 14 (or other dilator) may be confirmed using fluoroscopy, trans-illumination or other techniques in addition to visualization via the endoscope 60. The guide handle 42 may also be used to allow the operator to hold or support the guide catheter 40c (or the entire guide catheter/dilation catheter system) while keeping his hand a spaced distance away from the guide catheter shaft so as to avoid radiation exposure to his hand during use of the fluoroscope.

In embodiments where the handle member 48 is shapeable (e.g., malleable or bendable) the shape of the handle member 48 may be modified one or more times prior to or during the procedure to facilitate comfortable grasping of the handle by the operator's scope hand and/or to adjust the position or angle of the endoscope relative to the guide catheter. In this regard, in FIG. 8A, the handle member 48 is bent to a shape that results in a first angle A between the shaft of the guide catheter 40c and the endoscope 60, and the operator's other hand is being used to advance the guidewire GW through the lumen of the dilation catheter 10. In FIG. 8A, the handle has been modified to a different shape that results in a lesser angle A between the shaft of the guide catheter 40c and the endoscope 60, and the operator's other hand is being used to advance the dilation catheter 10 through the lumen of the guide catheter 40c.

The optional handle 42 may also be useful with other dilation catheters and other trans-nasal devices described in any or all of the parent applications of which this application is a continuation-in-part and/or those currently available commercially under the trademark Relieva from Acclarent, Inc., Menlo Park, Calif.

In some applications, the handle 42 may be designed to connect by way of a unique or proprietary connector to the guide catheter or other device. Or, in some embodiments, the handle 42 may be pre-attached, integrally formed with or otherwise designed as a part or portion of the guide catheter or other device. In embodiments where the handle 42 is not detachable from the guide catheter or other device, it may nonetheless be rotatable and/or lockable in a desire position Endoscopically Visible Markers and Anti-Glare Coatings An additional visible marker 19 may optionally be formed on the proximal end of the balloon 14 and/or on the distal shaft portion $12_{dist}$, such as at the location where the proximal end of the balloon 14 is bonded to the distal shaft portion $12_{dist}$.

These visible markers 19, 24, 26 are preferably of a color (e.g., black or blue) that contrasts with the pink color of the nasal mucosa so as to be easily visible within the nose. The optional marker 19 on the proximal end of the a balloon 14 allows the operator to endoscopically view the proximal end of the balloon even when the remainder of the balloon is within the ostium of a paranasal sinus. The other visible markers 24, 26 formed on the proximal shaft are specifically designed for use in conjunction with a guide catheter as will be discussed in detail herebelow.

In some cases, endoscopic images obtained of the markers or other portions of the guidewires GW, guide catheter 40a-40f or dilation catheter 10 may have areas of glare which can obscure visualization of certain portions of the markers or devices during performance of the procedure. To minimize such glare, an anti-glare (e.g., anti-reflective) treatment or coating may be applied to all or part of the sinus guide catheter 40a-40f, sinus guidewire GW and/or dilation catheter 10. Such anti-glare treatment could be applied by etching or sand-blasting and therefore does not add profile to the device. Such anti-glare coating could be applied by dip or spray coating and is very thin. The treatment or coating does not change the mechanical or functional properties of these devices. It may be selectively applied. For example, a black polytetrafluoroethylene (PTFE) coating on the sinus guidewire GW may provide good anti-reflective characteristics. Some of the commercially available anti-glare or anti-reflective coating can be applied. In some embodiments, an anti-glare surface treatment (e.g., roughening, etching, etc.) may be used or an anti-glare component such as a sheath, ring, paint, etc. may be used.

The advantages and benefits of including visible markers and/or the anti-glare coating include, improved endoscopic visualization, safer and easier performance of the procedure, reduced balloon burst or damage to critical structures, accuracy of placement of devices and reduced fluoroscopy time or elimination of fluoroscopy.

Modes of Use of the System

Figure 9:
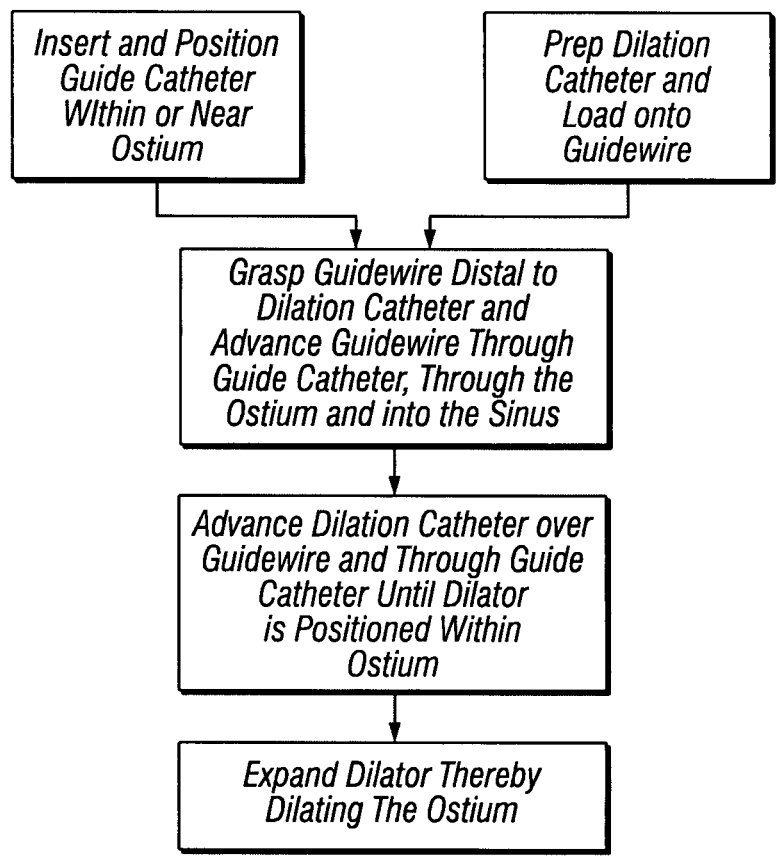
FIG. 9 is a flow diagram showing steps in one method for using a dilation catheter system of the present invention.
Figure 10:
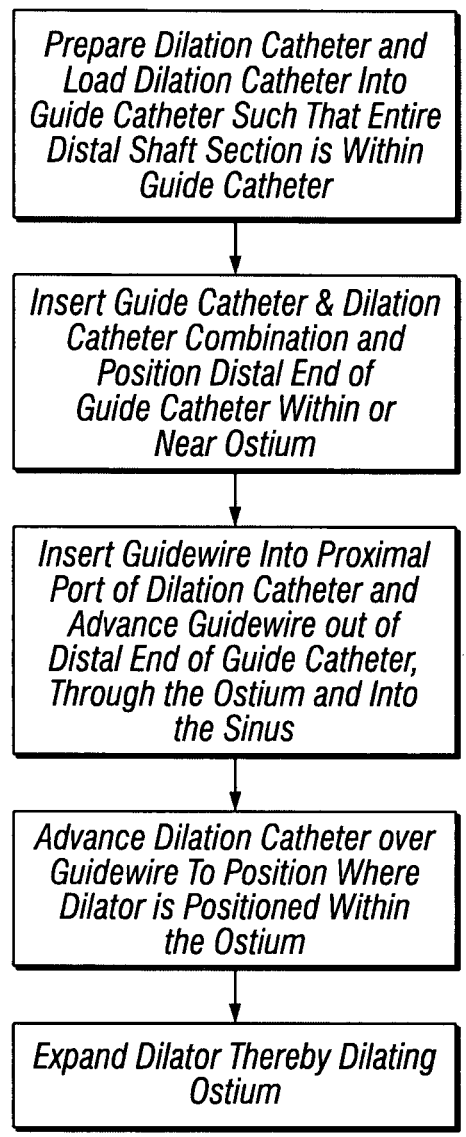
FIG. 10 is a flow diagram showing steps in another method for using a dilation catheter system of the present invention.
Figure 11:
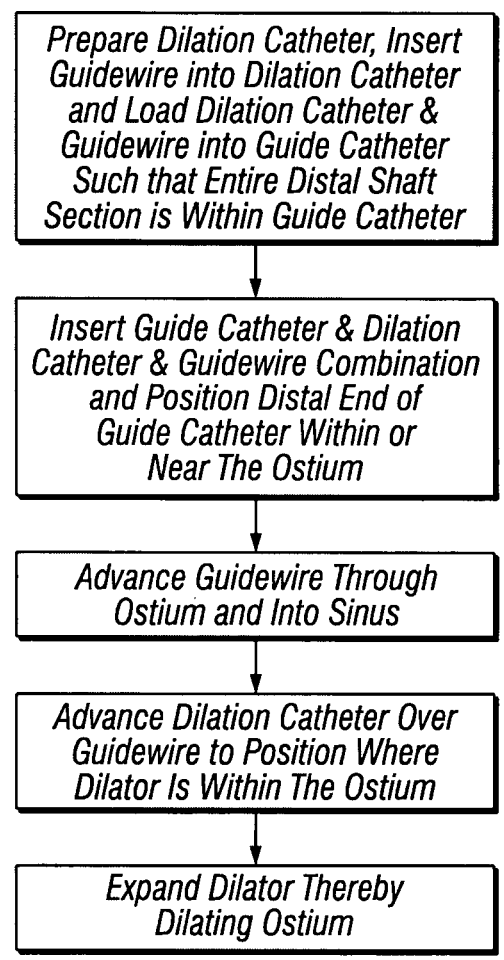
FIG. 11 is a flow diagram showing steps in yet another method for using a dilation catheter system of the present invention.

FIGS. 9-11 are flow diagrams describing three (3) modes of use by which the system of the present invention may be used to dilate the ostium of a paranasal sinus.

Mode 1—Inserting Guide Catheter, Guidewire and Dilation Catheter Separately

In the example of FIG. 9, the dilation catheter 10 is prepared for use separately from the guide catheter 40a-40f. The guide catheter 40a-40f is initially inserted (along with an endoscope 60) and is advanced to a position that is within or near the ostium to be dilated. An endoscope 60 is used to view the advancement and positioning of the guide catheter 40a-40f and fluoroscopy may also be used to verify that the guide catheter is properly positioned near or within the ostium. Optionally, a handle 42 may be attached to the guide catheter 40a-40f as described above or the operator may simply grasp the guide catheter 40a-40f as well as the endoscope 60 with the scope hand, thus leaving the operator's other hand free to be used for subsequent handling and manipulation of the other devices used in this procedure. Alternatively, a scope holder or assistant may be used to hold the endoscope 60 in the desired position thus freeing both of the operator's hands for handling and manipulation of the other devices.

After the guide catheter 40a-40f has been positioned, the operator will insert the distal end of the guidewire into the proximal end of the guide catheter 40a-40d and will advance the guidewire GW through the guide catheter 40a-40d such that a distal portion of the guidewire GW passes through the sinus ostium and becomes coiled within the sinus cavity. Fluoroscopy (or any other suitable technique) may be used to verify that the guidewire has become coiled within the intended sinus cavity.

Thereafter, the proximal end of the guidewire GW is inserted into the distal end of the dilation catheter 10 and the dilation catheter 10 (with its balloon 14 or other dilator in its non-expanded state) is advanced over the guidewire and through the guide catheter 40a-40d to a position where the dilator 14 is positioned within the sinus ostium. The endoscope 60 may be used to view the advancement and positioning of the dilation catheter 10. Although the distal portion of the balloon 14 or other dilator will be within the sinus and out of the field of view of the endoscope 60, the endoscope 60 may be used to view the proximal end of the balloon 14 or other dilator and/or the optional marker 19 (if present) on the proximal end of the balloon 14 or other dilator. Fluoroscopy may be used to image the radiographic markers 40, 42 and the ostium to confirm that the mid-region 44 of the balloon 14 (or the appropriate portion of any other type of dilator) is positioned within the ostium.

After the balloon 14 or other dilator has been positioned within the ostium, the balloon is inflated (or the other dilator is expanded) thereby dilating the ostium.

The balloon is then deflated (or the dilator is returned to its non-expanded state) and the successful dilation of the ostium may be confirmed visually using the endoscope 60 and/or radiographically using a fluoroscope.

Thereafter, the dilation catheter 10, guidewire GW and guide catheter 40a-40f are removed.

Mode 2—Preloading Dilation Catheter Into Guide Catheter Then Inserting Guidewire Separately In the example of FIG. 10, the dilation catheter 10 is prepared for use and is pre-inserted into the guide catheter 40a-40f to a position where the first shaft marker 24 is flush with the proximal end of the guide catheter. When so positioned all of the flexible distal shaft portion 12dist and a bit of the rigid proximal shaft portion 12prox will be within the guide catheter 40a-40f.

Thereafter, the guide catheter 40a-40f in combination with the pre-inserted dilation catheter 10 is inserted transnasally (along with an endoscope 60) and is advanced to a position that is within or near the ostium to be dilated. The endoscope 60 is used to view the advancement and positioning of the guide catheter 40a-40f and fluoroscopy may also be used to verify that the guide catheter is properly positioned near or within the ostium. Optionally, a handle 42 may be attached to the guide catheter 40a-40f as described above or the operator may simply grasp the guide catheter 40a-40f as well as the endoscope 60 with the scope hand, thus leaving the operator's other hand free to be used for subsequent handling and manipulation of the other devices used in this procedure. Alternatively, a scope holder or assistant may be used to hold the endoscope 60 in the desired position thus freeing both of the operator's hands for handling and manipulation of the other devices.

After the guide catheter 40a-40f and pre-inserted dilation catheter 10 have been positioned, the operator will insert the distal end of the guidewire into the proximal Luer 20 of the dilation catheter 10 and will advance the guidewire GW through the dilation catheter 10, out of the distal end of the guide catheter 40a-40d and through the sinus ostium, causing a distal portion of the guidewire to become coiled within the sinus cavity. Fluoroscopy (or any other suitable technique) may be used to verify that the guidewire has become coiled within the intended sinus cavity.

Thereafter, the dilation catheter 10 (with its balloon 14 or other dilator still in its non-expanded state) is advanced over the guidewire GW to a position where the balloon 14 or other dilator is positioned within the sinus ostium. The endoscope 60 may be used to view the advancement and positioning of the dilation catheter. Although the distal portion of the balloon 14 or other dilator will be within the sinus and out of the field of view of the endoscope 60, the endoscope 60 may be used to view the proximal end of the balloon 14 or other dilator and/or the optional marker 19 (if present) on the proximal end of the balloon 14 or other dilator. Fluoroscopy may be used to image the radiographic markers 40, 42 and the ostium to confirm that the midregion 44 of the balloon 14 (or the appropriate portion of any other type of dilator) is positioned within the ostium.

After the balloon 14 or other dilator has been positioned within the ostium, the balloon is inflated (or the other dilator is expanded) thereby dilating the ostium.

The balloon is then deflated (or the dilator is returned to its non-expanded state) and the successful dilation of the ostium may be confirmed visually using the endoscope 60 and/or radiographically using a fluoroscope.

Thereafter, the dilation catheter 10, guidewire GW and guide catheter 40a-40f are removed.

Mode 3—Preloading Guidewire and Dilation Catheter Into Guide Catheter

In the example of FIG. 11, the dilation catheter 10 is prepared for use and the distal end of the guidewire is pre-inserted into the proximal Luer 20 of the dilation catheter 10 and advanced to a position where the distal end of the guidewire is within protruding just slightly out of the distal end of the dilation catheter 10. The dilation catheter 10, with the pre-inserted guidewire GW, is pre-inserted into the guide catheter 40a-40f and advanced to a position where the first shaft marker 24 is flush with the proximal end of the guide catheter. When so positioned all of the flexible distal shaft portion $12_{dist}$ and a bit of the rigid proximal shaft portion $12_{prox}$ will be within the guide catheter 40a-40f.

Thereafter, the guide catheter 40a-40f with the dilation catheter 10 and guidewire pre-inserted therein is inserted through a nostril (along with an endoscope 60) and is advanced to a position that is within or near the ostium to be dilated. The endoscope 60 is used to view the advancement and positioning of the guide catheter 40a-40f and fluoroscopy may also be used to verify that the guide catheter is properly positioned near or within the ostium. Optionally, a handle 42 may be attached to the guide catheter 40a-40f as described above or the operator may simply grasp the guide catheter 40a-40f as well as the endoscope 60 with the scope hand, thus leaving the operator's other hand free to be used for subsequent handling and manipulation of the other devices used in this procedure. Alternatively, a scope holder or assistant may be used to hold the endoscope 60 in the desired position thus freeing both of the operator's hands for handling and manipulation of the other devices.

After the guide catheter 40a-40f and pre-inserted dilation catheter 10 and guidewire GW have been positioned, the operator will advance the guidewire out of the distal end of the guide catheter 40a-40f and through sinus ostium, causing a distal portion of the guidewire to become coiled within the sinus cavity. Fluoroscopy (or any other suitable technique) may be used to verify that the guidewire has become coiled within the intended sinus cavity.

Thereafter, the dilation catheter 10 (with its balloon 14 or other dilator still in its non-expanded state) is advanced over the guidewire GW to a position where the balloon 14 or other dilator is positioned within the sinus ostium. The endoscope 60 may be used to view the advancement and positioning of the dilation catheter. Although the distal portion of the balloon 14 or other dilator will be within the sinus and out of the field of view of the endoscope 60, the endoscope 60 may be used to view the proximal end of the balloon 14 or other dilator and/or the optional marker 19 (if present) on the proximal end of the balloon 14 or other dilator. Fluoroscopy may be used to image the radiographic markers 40, 42 and the ostium to confirm that the midregion 44 of the balloon 14 (or the appropriate portion of any other type of dilator) is positioned within the ostium.

After the balloon 14 or other dilator has been positioned within the ostium, the balloon is inflated (or the other dilator is expanded) thereby dilating the ostium.

The balloon is then deflated (or the dilator is returned to its non-expanded state) and the successful dilation of the ostium may be confirmed visually using the endoscope 60 and/or radiographically using a fluoroscope.

Thereafter, the dilation catheter 10, guidewire GW and guide catheter 40a-40f are removed.

Although the above described examples refer to use of a guide catheter 40a-40d and/or guidewire GW to guide the advancement of the dilation catheter 10 to its intended position within the ear, nose or throat, it is to be appreciated that in some subjects and/or in some applications, the dilation catheter may be advanceable or maneuverable to its intended position without the use of a guide catheter 40a-40f and/or guidewire GW. For example, in some subjects, the dilation catheter 10 may be advanced into the sphenoid sinus ostium without the use of a guidewire GW or guide catheter 40a-40d. Alternatively the flexible balloon portion may be manipulated with forceps to enable insertion in the ostium. Similar techniques may apply to access of the frontal and maxillary ostium.

The fact that the system described herein includes a guide catheter 40a-40f that is separate from the dilation catheter 10 has certain advantages. For example, by having two separate devices, the operator has separate control of the guide placement and may, in some cases, elect not to actually advance the guide into the ostium or recess before the ostium. Rather, the operator may in some instances elect to maneuver the guide catheter 40a-40f to a position that is close to (e.g., aligned with) but not within the ostium or recess, and may then advanced just the relatively flexible dilation catheter 10 into the ostium or recess. This may avoid damage tissue, bone or other anatomical structures. Thus, the use of a guide that is separate from the dilation catheter allows flexibility of positioning and potentially less trauma than where a single rigid device (e.g., a rigid shafted dilation catheter) must be navigated to the desired location and then actually inserted into the ostium or other passageway to be dilated.

It is to be appreciated that the invention has been described hereabove with reference to certain examples or embodiments of the invention but that various additions, deletions, alterations and modifications may be made to those examples and embodiments without departing from the intended spirit and scope of the invention. For example, any element or attribute of one embodiment or example may be incorporated into or used with another embodiment or example, unless otherwise specified of if to do so would render the embodiment or example unsuitable for its intended use. Also, where the steps of a method or process have been described or listed in a particular order, the order of such steps may be changed unless otherwise specified or unless doing so would render the method or process unworkable for its intended purpose. All reasonable additions, deletions, modifications and alterations are to be considered equivalents of the described examples and embodiments and are to be included within the scope of the following claims.

What is claimed is:

1. A system for treating a disease or disorder of the ear, nose or throat of a human or animal subject, said system comprising:

a guide catheter that is insertable into the head of the subject, said guide catheter having a substantially rigid shaft, a proximal opening, a distal opening and a lumen extending between the proximal opening and the distal opening;

a handle having bore, a portion of the handle being insertable into the proximal opening of the guide catheter such that the bore of the handle is in alignment with the lumen of the guide catheter;

a working catheter having a substantially rigid proximal shaft portion and a distal shaft portion that is sufficiently flexible to assume various shapes and a guidewire lumen;

a guidewire that is advanceable through the guidewire lumen;

a member attached to the guidewire to a) facilitate grasping of the guidewire, b) limit the extent to which the guidewire is advanceable through the guidewire lumen and c) hold the guidewire in a substantially fixed position relative to the working catheter when the guidewire has been fully advanced; and the working catheter being insertable through the bore of the handle and through the lumen of the guide catheter to a position where some of the distal shaft portion but none of the substantially rigid proximal portion extends out of the distal end of the guide catheter and some of the substantially rigid proximal shaft portion but none of the distal shaft portion extends out of the proximal end of the guide catheter.

2. A system according to claim 1 wherein the working catheter comprises dilation catheter and the working element comprises an expandable dilator that is positionable within a passageway of the ear, nose or throat and useable to dilate that passageway.

3. A system according to claim 2 wherein the expandable dilator comprises a balloon.

4. A system according to claim 2 wherein the expandable dilator is sized to be positioned within the ostium of a paranasal sinus while in a non-expanded state and to be thereafter expanded to an expanded state whereby it causes dilation of the ostium.

5. A system according to claim 4 wherein the working catheter is advanceable at least 2.5 cm beyond the distal end of the guide catheter.

6. A system according to claim 4 wherein the expandable dilator, when in its expanded state, has a diameter in the range of approximately 2.5 mm to approximately 10 mm.

7. A system according to claim 6 wherein the expandable dilator, when in its expanded state, has a diameter in the range of approximately 3.0 mm to approximately 7.0 mm.

8. A system according to claim 1 wherein the working catheter has an overall length of about 21 cm and wherein the substantially rigid proximal shaft portion of the working catheter is at least 12.5 cm in length.

9. A system according to claim 1 wherein the distal shaft portion of the working catheter is in the range between about 5 cm to about 9 cm in length.

10. A system according to claim 8 wherein the substantially rigid proximal shaft portion of the working catheter is about 12.5 cm in length and the distal shaft portion of the working catheter is about 8.7 cm in length.

11. A system according to any of claim 8, 9 or 10 wherein the distal shaft portion of the working catheter includes a distal tip member that extends distal to the working element and is more flexible than the distal shaft portion proximal to the working element.

12. A system according to claim 3 wherein the working catheter has a inflation fluid lumen through which inflation fluid passes into and out of the balloon and wherein that inflation fluid lumen is sized so that, after the balloon has been inflated to its working diameter, the balloon will deflate in les than about 15 seconds with application of negative pressure to the inflation fluid lumen by a conventional balloon catheter inflation and deflation device.

13. A system according to claim 3 wherein the working catheter has:

a inflation fluid lumen through which inflation fluid passes into and out of the balloon;

a guidewire lumen; and a proximal hub having an inflation port in communication with the inflation lumen and a guidewire port in communication with the guidewire lumen, said inflation port is substantially perpendicular to said guidewire port.

14. A system according to claim 13 wherein the guidewire port is on the proximal end of the hub and the inflation port is on a side of the hub.

15. A system according to claim 13 wherein the guidewire lumen has a lubricious coating or liner disposed therein.

16. A system according to claim 13 wherein the guidewire lumen is coated with a silicone coating.

17. A system according to claim 1 wherein the handle is graspable, along with another device, by a single hand of an operator.

18. A system according to claim 17 wherein the handle is graspable, along with an endoscope, by a single hand of an operator.

19. A system according to claim 1 further in combination with a stabilization device that is attachable to the guide catheter, said stabilization device facilitating control of the guide catheter and endoscope by a single hand of an operator.

20. A system according to claim 1 wherein at least a portion of the handle is shapeable so that it may be deformed to a desired bend or shape by the operator.

21. A system according to claim 1 wherein the member frictionally engages a hub on the working catheter.

22. A system according to claim 1 wherein the distal shaft portion is flexible.

23. A system according to claim 1 wherein the guide catheter is curved.

24. A system according to claim 1 wherein a distal portion of the guide catheter is curved.

25. A system according to claim 23 wherein the guide catheter has a curve in the range of 30 degrees to 110 degrees.

26. A system according to claim 1 wherein the distal shaft portion of the working catheter telescopes out the distal end of the guide catheter.

27. A system according to claim 1 further comprising a second member that is attachable to the working catheter and limits the extent to which the working catheter is advanceable through the guide catheter.

28. A system according to claim 27 wherein the member frictionally engages a hub on the working catheter and the second member frictionally engages a hub on the guide catheter.

29. A system according to claim 27 wherein the second member is permanently attached to the working catheter.

30. A system according to claim 1 wherein the member is permanently attached to the guide catheter.

* * * * *